United States Patent [19]

Ross et al.

[11] Patent Number: 5,498,722

[45] Date of Patent: Mar. 12, 1996

[54] BENZOFURAN DERIVATIVES

[75] Inventors: Barry C. Ross; David Middlemiss; David I. C. Scopes; Torquil I. M. Jack; Kevin S. Cardwell; Michael D. Dowle; Duncan B. Judd; Stephen P. Watson, all of Ware, Great Britain

[73] Assignee: Glaxo Group, London, England

[21] Appl. No.: 220,698

[22] Filed: Mar. 31, 1994

Related U.S. Application Data

[62] Division of Ser. No. 883,378, May 15, 1992, Pat. No. 5,332,831.

[30] Foreign Application Priority Data

May 16, 1991 [GB] United Kingdom ............. 9110636

[51] Int. Cl.$^6$ .................... C07D 407/12; C07D 407/14; A61K 31/415

[52] U.S. Cl. ........................................... 548/315.4

[58] Field of Search .................... 548/315.4; 514/397

[56] References Cited

U.S. PATENT DOCUMENTS

| | | | |
|---|---|---|---|
| 4,526,896 | 7/1985 | Scherrer et al. | 514/392 |
| 4,659,709 | 4/1987 | Harada et al. | 514/232 |
| 5,190,942 | 3/1993 | Poss | 514/235.8 |

FOREIGN PATENT DOCUMENTS

| | | |
|---|---|---|
| 0005528 | 11/1979 | European Pat. Off. . |
| 0028834 | 5/1981 | European Pat. Off. . |
| 0028833 | 5/1981 | European Pat. Off. . |
| 0069521 | 1/1983 | European Pat. Off. . |
| 0253310 | 1/1988 | European Pat. Off. . |
| 0380959 | 8/1990 | European Pat. Off. . |
| 0403159 | 12/1990 | European Pat. Off. . |
| 0425211A1 | 5/1991 | European Pat. Off. . |
| 0427463A1 | 5/1991 | European Pat. Off. . |
| 0434249A2 | 6/1991 | European Pat. Off. . |
| WO9100281 | 1/1991 | WIPO . |
| WO91/00277 | 1/1991 | WIPO . |

Primary Examiner—David B. Springer
Attorney, Agent, or Firm—Bacon & Thomas

[57] ABSTRACT

The invention provides compounds of formula (I):

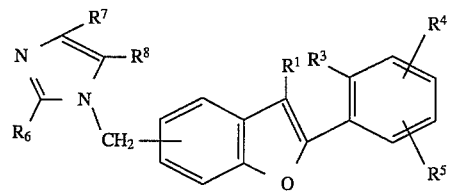

or a physiologically acceptable salt, solvate or metabolically labile ester thereof wherein the R groups are defined in the specification.

The compounds may be used in the treatment or prophylaxis of hypertension and diseases associated with cognitive disorders.

16 Claims, No Drawings

BENZOFURAN DERIVATIVES

This application is a Division of application Ser. No. 07/883,378, filed May 15, 1992, now allowed as U.S. Pat. No. 5,532,831.

This invention relates to benzofuran derivatives, processes for their preparation and pharmaceutical compositions containing them. According to a first aspect of the invention we provide a compound of the general formula (I):

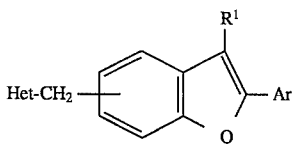

or a physiologically acceptable salt, solvate (e.g. hydrate) or metabolically labile ester thereof in which $R^1$ represents a hydrogen atom or a halogen atom or a group selected from $C_{1-6}$alkyl, $C_{2-6}$alkenyl, fluoro$C_{1-6}$alkyl, $C_{1-6}$alkoxy, —CHO, —$CO_2H$ or —$COR^2$;

Ar represents the group

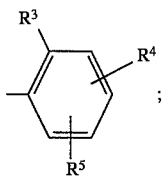

$R^2$ represents a group selected from $C_{1-6}$alkyl, $C_{2-6}$alkenyl, $C_{1-6}$alkoxy or the group —$NR^{13}R^{14}$;

$R^3$ represents a group selected from —$CO_2H$, —$NHSO_2CF_3$ or a C-linked tetrazolyl group;

$R^4$ and $R^5$ which may be the same or different each independently represent a hydrogen atom or a halogen atom or a $C_{1-6}$alkyl group;

Het represents the group

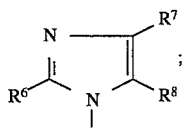

$R^6$ represents a hydrogen atom or a group selected from $C_{1-6}$alkyl, $C_{2-6}$alkenyl, $C_{1-6}$alkylthio, $C_{1-6}$alkoxy, $C_{3-7}$cycloalkyl or $C_{3-7}$cycloalkyl$C_{1-4}$alkyl;

$R^7$ represents a hydrogen atom or a halogen atom or a group selected from cyano, nitro, $C_{1-6}$alkyl, $C_{2-6}$alkenyl, fluoro$C_{1-6}$alkyl, —$(CH_2)_mR^9$, —$(CH_2)_nCOR^{10}$, —$(CH_2)_pNR^{11}COR^{12}$, $C_{3-7}$cycloalkyl or $C_{3-7}$cycloalkyl$C_{1-4}$alkyl;

$R^8$ represents a hydrogen atom or a halogen atom or a group selected from cyano, nitro, $C_{1-6}$alkyl, $C_{2-6}$alkenyl, fluoro$C_{1-6}$alkyl, —$(CH_2)_mR^9$, —$(CH_2)_nCOR^{10}$ or —$(CH_2)_pNR^{11}COR^{12}$;

$R^9$ represents a hydroxy or $C_{1-6}$alkoxy group;

$R^{10}$ represents a hydrogen atom or a group selected from hydroxy, $C_{1-6}$alkyl, $C_{1-6}$alkoxy, phenyl, phenoxy or the group —$NR^{13}R^{14}$;

$R^{11}$ represents a hydrogen atom or a $C_{1-6}$alkyl group;

$R^{12}$ represents a hydrogen atom or a group selected from $C_{1-6}$alkyl, $C_{1-6}$alkoxy, phenyl, phenoxy or the group —$NR^{13}R^{14}$;

$R^{13}$ and $R^{14}$, which may be the same or different, each independently represent a hydrogen atom or a $C_{1-4}$alkyl group or —$NR^{13}R^{14}$ forms a saturated heterocyclic ring which has 5 or 6 ring members and may optionally contain in the ring one oxygen atom;

m represents an integer from 1 to 4, preferably 1 or 2, especially 1;

n represents zero or an integer from 1 to 4, preferably zero, 1 or 2, especially zero or 1; and p represents an integer from 1 to 4, preferably 1 or 2; with the proviso that when $R^6$ represents a hydrogen atom or a group selected from $C_{1-6}$alkyl, $C_{2-6}$alkenyl or $C_{1-6}$alkylthio, $R^7$ represents a group selected from $C_{3-7}$cycloalkyl or $C_{3-7}$cycloalkyl$C_{1-4}$alkyl.

In a further or alternative aspect of the present invention, $R^{13}$ and $R^{14}$, which may be the same or different, each independently represent, in addition to those groups defined above in general formula (I), a group selected from $C_{5-6}$alkyl, fluoro$C_{1-6}$alkyl, $C_{3-7}$cycloalkyl, $C_{3-7}$cycloalkyl$C_{1-4}$alkyl, —$(CH_2)_qR^{15}$ or —$SO_2R^{15}$, wherein $R^{15}$ represents an aryl group such as a phenyl or pyridinyl group and q represents an integer from 1 to 4, preferably 1 or 2, especially 1.

Where a compound of general formula (I) is optically active, said formula (I) is intended to cover all enantiomers, diastereoisomers and mixtures thereof including racemates. Where a compound of the present invention contains one or more double bonds, these may exist in the cis or trans configuration. Furthermore, where such geometric isomers exist, formula (I) is intended to cover mixtures thereof.

The invention also includes within its scope the solvates, especially the hydrates of compounds of general formula (I).

Within the above definition the term 'alkyl' 'alkoxy' or 'alkylthio' as a group or part of a group means that the group is straight or branched. The term 'alkenyl' as a group or part of a group means that the group is straight or branched and contains at least one carbon—carbon double bond. The term 'cycloalkyl' as a group or part of a group may be, for example, a cyclopropyl, cyclobutyl, cyclopentyl or cyclohexyl group.

The term 'halogen' means a fluorine, chlorine, bromine or iodine atom.

The term 'fluoro$C_{1-6}$alkyl' means a $C_{1-6}$alkyl group in which one or more hydrogen atoms have been replaced by a fluorine atom, for example, —$CH_2CF_3$. Particularly preferred are 'perfluoro$C_{1-3}$alkyl' groups meaning a fully fluorinated $C_{1-3}$alkyl group, i.e. trifluoromethyl, pentafluoroethyl, heptafluoropropyl or heptafluoroisopropyl.

Within the above definition when —$NR^{13}R^{14}$ represents a saturated heterocyclic ring, this contains 5 or 6 ring members, one of which may be an oxygen atom. Suitable heterocyclic groups are a pyrrolidino, piperidino or morpholino group.

A preferred class of compounds of general formula (I) is that wherein $R^6$ is a hydrogen atom, a $C_{1-5}$alkyl, especially a $C_{2-5}$alkyl, group, a $C_{3-5}$alkenyl group, a $C_{1-6}$alkoxy group, a $C_{3-7}$cycloalkyl group or a $C_{3-7}$cycloalkyl$C_{1-4}$alkyl group. Particularly preferred substituents are an ethyl, n-propyl, or n-butyl, especially an ethyl, group, a but-1-enyl group, an ethoxy group, a cyclopropyl or cyclobutyl group or a cyclopropylmethyl group.

Another preferred class of compounds of general formula (I) is that wherein $R^7$ is a halogen atom or a group selected from $C_{1-6}$alkyl, $C_{3-7}$cycloalkyl or $C_{3-7}$cycloalkyl$C_{1-4}$alkyl.

In particular, $R^7$ represents a chlorine atom or a methyl, ethyl, propyl, cyclopropyl, cyclobutyl or cyclopropylmethyl group.

Another preferred class of compounds of general formula (I) is that wherein $R^8$ represents a group selected from —$(CH_2)_m R^9$ or —$(CH_2)_n COR^{10}$. In particular, $R^9$ represents a hydroxy or $C_{1-6}$alkoxy group, and preferably a hydroxy, methoxy, ethoxy, propoxy, or butoxy, group, and especially a hydroxy or methoxy group. $R^{10}$, in particular, represents a hydrogen atom or a hydroxy, $C_{1-6}$alkoxy or —$NR^{13}R^{14}$ group (especially wherein $R^{13}$ and $R^{14}$ each independently represent a hydrogen atom or a $C_{1-4}$alkyl group), and preferably a hydrogen atom or a hydroxy, methoxy, ethoxy, propoxy, butoxy, amino, methylamino or ethylamino group, and especially a hydrogen atom or a hydroxy, methoxy, amino, methylamino or ethylamino group. Preferably m is 1 or 2, and n is zero, 1 or 2 especially zero or 1, most especially zero.

In particularly preferred embodiments of the present invention, $R^6$ represents an ethoxy, cyclopropyl, cyclobutyl or cyclopropylmethyl group, $R^7$ represents a chlorine atom or a methyl or ethyl group and $R^8$ represents a group selected from —$CH_2OH$, —$CHO$, —$CH_2OCH_3$, —$CO_2H$, —$CO_2CH_3$, —$CO_2CH_2CH_3$, —$CONH_2$, —$CONHCH_3$ or —$CONHCH_2CH_3$.

In a further particularly preferred embodiment of the present invention $R^6$ represents a $C_{1-5}$alkyl group such as an ethyl or propyl group, $R^7$ represents a cyclopropyl, cyclobutyl or cyclopropylmethyl group and $R^8$ represents a group selected form $CH_2OH$, $CHO$, $CH_2OCH_3$, $CO_2H$, $CO_2CH_3$, $CO_2CH_2CH_3$, $CONH_2$, $CONHCH_3$ or $CONHCH_2CH_3$.

A yet further preferred class of compounds of general formula (I) is that wherein $R^1$ represents a hydrogen atom or a halogen atom or a group selected from $C_{1-6}$alkyl, $C_{1-6}$alkoxy or fluoro$C_{1-6}$alkyl, and in particular a hydrogen atom or halogen atom or a $C_{1-3}$alkyl group. Especially preferred are compounds wherein $R^1$ is a bromine atom.

Conveniently, in the compounds of general formula (I), the group Het—$CH_2$— is attached at the 5- or 6-position on the benzofuran ring, and especially the 5-position.

Still conveniently, in the compounds of general formula (I), $R^4$ and $R^5$ may each independently represent a hydrogen atom or a halogen atom. In particular $R^4$ and $R^5$ each represent hydrogen atoms.

Particularly preferred compounds of the invention include:

1-[[3-Bromo-2-[2-(1H-tetrazol-5-yl)phenyl]-5-benzofuranyl]methyl]- 2-cyclopropyl-4-methyl-1H-imidazole-5-carboxylic acid;

1-[[3-Bromo-2-[2-[[(trifluoromethyl)sulphonyl]amino]phenyl]-5-benzofuranyl] methyl]-2-cyclopropyl-4-methyl-1H-imidazole-5-carboxamide;

1-[[3-Bromo-2-[2-[[(trifluoromethyl)sulphonyl]amino]phenyl]-5-benzofuranyl] methyl]-2-cyclopropyl-N,4-dimethyl-1H-imidazole-5-carboxamide;

1-[[3-Bromo-2-[2-[[(trifluoromethyl)sulphonyl]amino]phenyl]-5-benzofuranyl] methyl]-2-cyclopropyl-N-ethyl-4-methyl-1H-imidazole-5-carboxamide;

1-[[3-Bromo-2-[2-(1H-tetrazol-5-yl)phenyl]-5-benzofuranyl]methyl]- 4-chloro-2-cyclopropyl-1H-imidazole-5-carboxylic acid;

1-[[3-Bromo-2-[2-[[(trifluoromethyl)sulphonyl]amino]phenyl]-5-benzofuranyl] methyl]-4-chloro-2-cyclopropyl-1H-imidazole-5-carboxamide;

1-[[3-Bromo-2-[2-[[(trifluoromethyl)sulphonyl]amino]phenyl]-5-benzofuranyl] methyl]-4-chloro-2-cyclopropyl-N-methyl-1H-imidazole-5-carboxamide;

1-[[3-Bromo-2-[2-[[(trifluoromethyl)sulphonyl]amino]phenyl]-5-benzofuranyl] methyl]-4-chloro-2-cyclopropyl-N-ethyl-1H-imidazole-5-carboxamide;

1-[[3-Bromo-2-[2-(1H-tetrazol-5-yl)phenyl]-5-benzofuranyl]methyl]- 2-cyclopropylmethyl-4-methyl-1H-imidazole-5-carboxylic acid;

1-[[3-Bromo-2-[2-[[(trifluoromethyl)sulphonyl]amino]phenyl]-5-benzofuranyl] methyl]-2-cyclopropylmethyl-4-methyl-1H-imidazole-5-carboxamide;

1-[[3-Bromo-2-[2-[[(trifluoromethyl)sulphonyl]amino]phenyl]-5-benzofuranyl] methyl]-2-cyclopropylmethyl-N,4-dimethyl-1H-imidazole- 5-carboxamide;

1-[[3-Bromo-2-[2-[[(trifluoromethyl)sulphonyl]amino]phenyl]-5-benzofuranyl] methyl]-2-cyclopropylmethyl-N-ethyl-4-methyl-1H-imidazole- 5-carboxamide;

1-[[3-Bromo-2-[2-(1H-tetrazol-5-yl)phenyl]-5-benzofuranyl]methyl]- 4-chloro-2-cyclopropylmethyl-1H-imidazole-5-carboxylic acid;

1-[[3-Bromo-2-[2-[[(trifluoromethyl)sulphonyl]amino]phenyl]- 5-benzofuranyl]methyl]-4-chloro-2-cyclopropylmethyl-N-methyl-1H-imidazole- 5-carboxamide;

1-[[3-Bromo-2-[2-[[(trifluoromethyl)sulphonyl]amino]phenyl]- 5-benzofuranyl]methyl]-4-chloro-2-cyclopropylmethyl-N-ethyl-1H-imidazole- 5-carboxamide;

1-[[3-Bromo-2-[2-[[(trifluoromethyl)sulphonyl]amino]phenyl]- 5-benzofuranyl]methyl]-4-chloro-2-cyclopropylmethyl-1H-imidazole-5-carboxamide;

1-[[3-Bromo-2-[2-(1H-tetrazol-5-yl)phenyl]-5-benzofuranyl]methyl]- 2-ethoxy-4-methyl-1H-imidazole-5-carboxylic acid;

1-[[3-Bromo-2-[2-[[(trifluoromethyl)sulphonyl]amino]phenyl]- 5-benzofuranyl]methyl]-2-ethoxy-4-methyl-1H-imidazole-5-carboxamide;

1-[[3-Bromo-2-[2-[[(trifluoromethyl)sulphonyl]amino]phenyl]- 5-benzofuranyl]methyl]-2-ethoxy-N,4-dimethyl-1H-imidazole-5-carboxamide;

1-[[3-Bromo-2-[2-[[(trifluoromethyl)sulphonyl]amino]phenyl]- 5-benzofuranyl]methyl]-2-ethoxy-N-ethyl-4-methyl-1H-imidazole-5-carboxamide;

1-[[3-Bromo-2-[2-(1H-tetrazol-5-yl)phenyl]-5-benzofuranyl]methyl]- 4-chloro-2-ethoxy-1H-imidazole-5-carboxylic acid;

1-[[3-Bromo-2-[2-[[(trifluoromethyl)sulphonyl]amino]phenyl]- 5-benzofuranyl]methyl]-4-chloro-2-ethoxy-1H-imidazole-5-carboxamide;

1-[[3-Bromo-2-[2-[[(trifluoromethyl)sulphonyl]amino]phenyl]- 5-benzofuranyl]methyl]-4-chloro-2-ethoxy-N-methyl-1H-imidazole-5-carboxamide;

1-[[3-Bromo-2-[2-[[(trifluoromethyl)sulphonyl]amino]phenyl]- 5-benzofuranyl]methyl]-4-chloro-2-ethoxy-N-ethyl-1H-imidazole-5-carboxamide;

1-[[3-Bromo-2-[2-[[(trifluoromethyl)sulphonyl]amino]phenyl]- 5-benzofuranyl]methyl]-4-cyclopropylmethyl-2-ethyl-1H-imidazole-5-carboxamide;

1-[[3-Bromo-2-[2-[[(trifluoromethyl)sulphonyl]amino]phenyl]- 5-benzofuranyl]methyl]-4-cyclopropylmethyl-2-ethyl-N-methyl-1H-imidazole-5-carboxamide;

1-[[3-Bromo-2-[2-[[(trifluoromethyl)sulphonyl]amino]phenyl]-5-benzofuranyl] methyl]-4-cyclopropylmethyl-N,2-diethyl-1H-imidazole-5-carboxamide;

1-[[3-Bromo-2-[2-[[(trifluoromethyl)sulphonyl]amino]phenyl]-5-benzofuranyl] methyl]-4-cyclobutyl-2-ethyl-1H-imidazole-5-carboxamide;

1-[[3-Bromo-2-[2-[[(trifluoromethyl)sulphonyl]amino]phenyl]-5-benzofuranyl] methyl]-4-cyclobutyl-2-ethyl-N-methyl-1H-imidazole-5-carboxamide;

1-[[3-Bromo-2-[2-[[(trifluoromethyl)sulphonyl]amino]phenyl]-5-benzofuranyl] methyl]-4-cyclobutyl-N,2-diethyl-1H-imidazole-5-carboxamide;

1-[[3-Bromo-2-[2-(1H-tetrazol-5-yl)phenyl]-5-benzofuranyl]methyl]- 4-cyclopropyl-2-ethyl-1H-imidazole-5-carboxylic acid;

1-[[3-Bromo-2-[2-(1H-tetrazol-5-yl)phenyl]-5-benzofuranyl]methyl]- 4-cyclobutyl-2-ethyl-1H-imidazole-5-carboxylic acid;

1-[[3-Bromo-2-[2-(1H-tetrazol-5-yl)phenyl]-5-benzofuranyl]methyl]- 4-cyclopropylmethyl-2-ethyl-1H-imidazole-5-carboxylic acid;

1-[[3-Bromo-2-[2-[[(trifluoromethyl)sulphonyl]amino]phenyl]-5-benzofuranyl] methyl]-4-cyclopropyl-2-ethyl-N-methyl-1H-imidazole-5-carboxamide;

1-[[3-Bromo-2-[2-[[(trifluoromethyl)sulphonyl]amino]phenyl]-5-benzofuranyl] methyl]-4-cyclopropyl-2-ethyl-1H-imidazole-5-carboxamide;

1-[[3-Bromo-2-[2-[[(trifluoromethyl)sulphonyl]amino]phenyl]-5-benzofuranyl] methyl]-4-cyclopropyl-N,2-diethyl-1H-imidazole-5-carboxamide;

and physiologically acceptable salts, solvates and metabolically labile esters thereof.

The physiologically acceptable acid addition salts of the compounds of formula (I) may be derived from inorganic or organic acids. Examples of such salts include hydrochlorides, hydrobromides, sulphates, phosphates, benzoates, methanesulphonates or trifluoroacetates.

The compounds may also form salts with suitable bases. Examples of such salts are alkali metal (e.g. sodium or potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, tetralkylammonium, piperidinium, ethylenediammonium and choline).

It will be appreciated that, for pharmaceutical use, the salts referred to above will be physiologically acceptable, but other salts may find use, for example, in the preparation of the compounds of formula (I) and the physiologically acceptable salts thereof.

It will be further appreciated that the compounds of general formula (I) may be chemically modified in the form of compounds which in vivo (for example, by enzymic attack) will provide the parent compounds of general formula (I). Such prodrugs may be, for example, physiologically acceptable metabolically labile ester derivatives. These may be formed by esterification, for example of any of the carboxylic acid groups in the parent compound of general formula (I), with prior protection of any other reactive groups present in the molecule. Examples of such esters include lower alkyl esters (e.g. methyl or ethyl esters), alkenyl esters (e.g. vinyl or allyl esters), alkynyl esters (e.g. ethynyl or propynyl esters), alkoxyalkyl esters, (e.g. methoxymethyl or 2-methoxyethyl esters), alkylthioalkyl esters (e.g. methylthiomethyl esters) haloalkyl esters (e.g. 2-iodoethyl or 2,2,2-trichloroethyl esters), alkanoyloxyalkyl esters (e.g. acetoxymethyl, 1-acetoxyethyl or pivaloyloxymethyl esters), alkoxycarbonyloxyalkyl esters (e.g. 1-ethoxycarbonyloxyethyl or 1-methoxycarbonyloxyethyl esters), aroyloxyalkyl esters (e.g. benzoyloxymethyl or 1-benzoyloxyethyl esters), substituted or unsubstituted aralkyl esters (e.g. benzyl or 4-amidobenzyl esters), substituted or unsubstituted aminoalkyl esters (e.g. aminoethyl or 2-N,N-dimethylaminoethyl esters) or hydroxyalkyl esters (e.g. 2-hydroxyethyl or 2,3-dihydroxypropyl esters).

In addition to the above ester derivatives the present invention includes within its scope compounds of general formula (I) in the form of other physiologically acceptable equivalents, i.e. physiologically acceptable compounds which, like the metabolically labile esters, are converted in vivo into the parent compounds of general formula (I).

According to a second aspect of the present invention we provide a compound of formula (I) or a physiologically acceptable salt, solvate or metabolically labile ester thereof for use in therapy.

In particular, the compounds of the present invention may be used in the treatment or prophylaxis of hypertension (for example, essential, malignant or resistant, caused by oral contraceptives, coarctation of the aorta or renal vascular disease) and pulmonary hypertension.

The compounds of the present invention may also be used in the treatment or prophylaxis of congestive heart failure, acute or chronic heart failure, aortic or cardiac insufficiency, post-myocardial infarction, renal insufficiency and renal failure (for example, as a result of diabetic nephropathy, glomerular nephritis, scleroderma or renal crisis), proteinuria, Bartter's syndrome, secondary hyperaldosteronism, Reynaud's syndrome, cerebrovascular insufficiency, peripheral vascular disease, diabetic retinopathy, atherogenesis and for the improvement of vascular compliance.

They are also potentially useful for the treatment of cognitive disorders such as dementia (e.g. Alzheimer's disease) and other CNS disorders, such as anxiety disorders, schizophrenia, depression and alcohol or drug (e.g. cocaine) dependency.

According to a further aspect of the present invention we provide a compound of formula (I) or a physiologically acceptable salt, solvate or metabolically labile ester thereof for use in the treatment of the aforementioned diseases, especially hypertension.

According to another aspect of the present invention we provide a compound of formula (I) or a physiologically acceptable salt, solvate or metabolically labile ester thereof for the manufacture of a therapeutic agent for the treatment of the aforementioned diseases, especially hypertension.

According to a further aspect of the present invention we provide a method of treating the aforementioned diseases, especially hypertension, which method comprises administering an effective amount to a patient in need of such treatment of a compound of formula (I) or a physiologically acceptable salt, solvate or metabolically labile ester thereof.

It will be appreciated that the compounds of formula (I) or a physiologically acceptable salt, solvate, or metabolically labile ester thereof may advantageously be used in conjunction with one or more other therapeutic agents, such as for example diuretics and/or different antihypertensive agents such as β-blockers, calcium channel blockers or ACE inhibitors. It is to be understood that such combination therapy constitutes a further aspect of the present invention.

It will be further appreciated that reference herein to treatment extends to prophylaxis as well as to the treatment and relief of established symptoms.

While it is possible that a compound of general formula (I) may be administered as the raw chemical it is preferable to present the active ingredient as a pharmaceutical formulation.

The compounds of formula (I) and their physiologically acceptable salts, solvates and metabolically labile esters may be formulated for administration in any convenient way, and the invention also includes within its scope pharmaceutical compositions comprising at least one compound of formula (I) or a physiologically acceptable salt, solvate or metabolically labile ester thereof adapted for use in human or veterinary medicine. Such compositions may be presented for use in conventional manner in admixture with one or more physiologically acceptable carriers or excipients. The carrier(s) must be 'acceptable' in the sense of being compatible with the other ingredients of the formulation and not deleterious to the recipient thereof.

Thus, the compounds according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

It will be appreciated that both tablets and capsules may be manufactured in the form of sustained release formulations, such that they provide a controlled continuous release of the compounds according to the invention over a period of hours.

The compounds of formula (I) and their physiologically acceptable salts, solvates and metabolically labile esters may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoro methane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, when the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 g which may be administered in 1 to 4 daily doses.

The compounds of the invention may be prepared by a number of processes as described below wherein the various groups are as defined for general formula (I) unless otherwise specified.

Thus, according to a further aspect of the present invention we provide a process (A) for preparing the compounds of general formula (I) which comprises treating a compound of general formula (II)

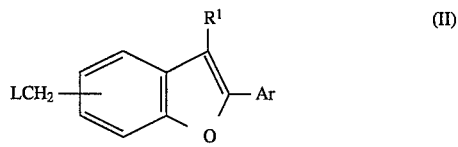

(wherein L is a leaving group, for example a halogen atom such as chlorine, bromine or iodine, or an alkyl- or arylsulphonyloxy group such as methanesulphonyloxy, or p-toluenesulphonyloxy and $R^1$ and Ar are as defined in general formula (I)) with an imidazole of general formula (III)

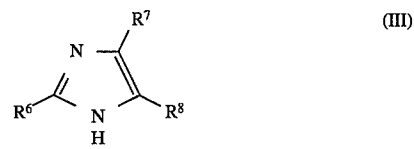

(wherein $R^6$, $R^7$ and $R^8$ are as defined in general formula (I)) followed by the removal of any protecting groups where present, as described hereinafter.

The preparation of compounds of general formula (I) wherein $R^6$ represents a $C_{1-6}$alkoxy group may also be effected by treating a compound of general formula (II) with an imidazole of general formula (IIIa)

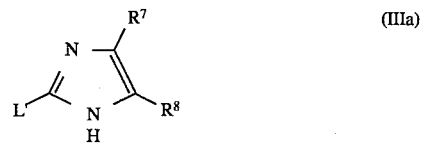

(wherein L' is a leaving group that is displaceable by an alkoxy group under conditions suitable for aromatic nucleophilic substitution) to give a compound of general formula (I) wherein $R^6$ is L'. This compound (general formula (I), $R^6$ is L') may be converted into a compound of general formula I wherein $R^6$ represents a $C_{1-6}$alkoxy group by treatment with an appropriate alkoxide.

In both of the above cases, the reaction of the compound of general formula (II) with the imidazole of general formula (III) or (IIIa) is preferably effected under basic conditions, for example, in the presence of sodium hydride, potassium carbonate or sodium methoxide. The reaction is conveniently effected in a solvent such as acetonitrile or an ether e.g. tetrahydrofuran or dioxan, a ketone e.g. butanone or methyl isobutyl ketone, or a substituted amide e.g. dimethylformamide, at a temperature between 0° C. and the reflux temperature of the solvent.

In another general process (B) a compound of general formula (I) may be obtained by deprotection of a protected intermediate of general formula (IV)

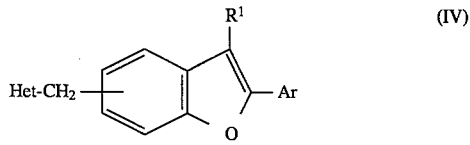

(wherein $R^1$, Ar and Het are as defined in general formula (I) except that at least one reactive group is blocked by a protecting group).

The protecting groups may be any conventional protecting groups, for example as described in "Protective Groups in Organic Synthesis" by Theodora Greene (John Wiley and Sons Inc., 1981). Examples of carboxyl protecting groups include $C_{1-6}$ alkyl such as methyl or t-butyl, or $C_{7-10}$aralkyl such as benzyl.

When $R^3$ is a tetrazole group, this may be protected with, for example, the trityl group —C(phenyl)$_3$, or a p-nitrobenzyl or 1-ethoxyethyl group.

Deprotection to yield the compound of general formula (I) may be effected using conventional techniques. Thus, for example, aralkyl groups may be cleaved by hydrogenolysis in a suitable organic solvent such as an alcohol, e.g. ethanol, in the presence of a noble metal catalyst such as palladium or platinum or an oxide thereof on a support such as charcoal, and conveniently at room temperature and pressure. Carboxyl protecting groups such as alkyl groups may be cleaved by hydrolysis using a base such as an alkali metal hydroxide (e.g. sodium hydroxide or potassium hydroxide) in a suitable solvent (e.g. an aqueous alcohol such as methanol or ethanol) at any suitable temperature up to reflux. Deprotection of the tetrazole group when protected with a trityl group may be effected by acid hydrolysis using trifluoroacetic acid or a mineral acid such as hydrochloric acid optionally in a suitable solvent such as ethanol conveniently at room temperature. Alternatively, when possible, deprotection of the tetrazolyl group can be effected by catalytic hydrogenation as previously described.

In another general process (C) a compound of general formula (I) in which the substituent $R^3$ in the group Ar represents a C-linked tetrazolyl group (and the imidazolyl group represented by Het is not substituted by a cyano group), may also be prepared from a compound of general formula (Ia)

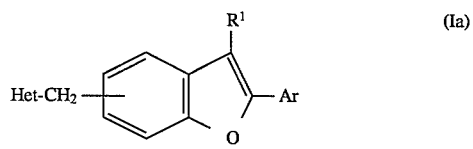

(wherein $R^1$, Ar and Het are as defined in general formula (I) except that in the group Ar, $R^3$ represents a nitrile group) by reaction with a suitable azide such as sodium azide, ammonium azide (preferably prepared in situ from sodium azide and ammonium chloride), trialkyl-(e.g. triethyl) ammonium azide (preferably prepared in situ from sodium azide and a trialkylamine salt (e.g. triethylamine hydrochloride)) or tributyl tin azide. The reaction is conveniently effected in a solvent such as xylene at an elevated temperature, such as the reflux temperature of the solvent, for between 1 and 10 days. Where the azide is tributyl tin azide the reaction may conveniently be effected in the absence of a solvent at a temperature between room temperature and 180° C. Such a reaction leaves the tetrazolyl group protected with a tributyl tin group, which can readily be removed using aqueous base or acid. Where aqueous base is used to effect this deprotection, the compound may be treated with an aqueous acid to liberate the free tetrazole.

Compounds of general formula (Ia) may be prepared by processes analogous to those described herein commencing from a compound of formula (VIII) and a corresponding benzofuran intermediate.

The intermediate compounds of general formula (Ia) and their acid addition salts are novel compounds and form a further aspect of the present invention.

In another general process (D) a compound of general formula (I) in which the substituent $R^3$ in the group Ar represents —NHSO$_2$CF$_3$, may also be prepared from a compound of general formula (Ib)

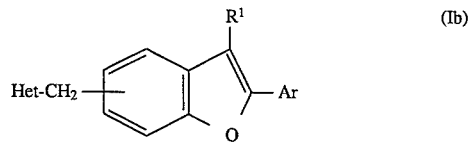

(wherein $R^1$, Ar and Het are as defined in general formula (I) except that in the group Ar, $R^3$ represents an amino group) by reaction with trifluoromethanesulphonic anhydride or trifluoromethylsulphonyl chloride, in a suitable solvent such as a halogenated hydrocarbon e.g. chloroform or dichloromethane in the presence of a base, e.g. triethylamine.

Compounds of general formula (Ib) may be prepared by processes analogous to those described herein commencing from a compound of formula (IX) and a corresponding benzofuran intermediate.

Alternatively, compounds of general formula (Ib) may be prepared by a Curtius rearrangement of a compound of formula (I) wherein $R^3$ in the group Ar is —CO$_2$H (provided that this is the only carboxylic acid group in the molecule) using, for example, diphenylphosphorylazide in the presence of a base such as triethylamine and in a solvent such as an alcohol (e.g. tert-butanol) to form a carbamate followed by deprotection of the amine in a conventional manner, for example by acid hydrolysis using hydrochloric acid in a solvent such as ethanol.

Compounds of general formula (Ib) may also be prepared by reduction of the corresponding nitro precursor using a reducing agent such as iron, tin or zinc in the presence of acid, for example, hydrochloric acid or acetic acid. The reaction is conveniently effected in a suitable solvent such as an alcohol (e.g. ethanol), water or a mixture thereof, at a temperature between room temperature and the reflux temperature of the solvent.

The nitro precursors are readily prepared using method analogous to those described herein.

The intermediate compounds of general formula (Ib), their nitro precurors and their acid addition salts are novel compounds and form a further aspect of the present invention.

In another general process (E) a compound of general formula (I), in which $R^8$ represents the group —CONHR$^{13}$, may be prepared by reaction of a compound of formula (XIII)

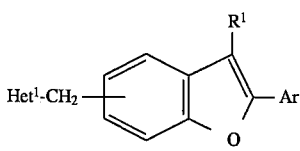

(wherein Het¹ represents a group of formula

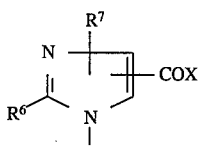

in which $R^6$ and $R^7$ are as defined in general formula (I) and X is a halogen atom (for example chlorine or bromine), or a hydroxyl or $C_{1-6}$alkoxy (for example, methoxy, ethoxy or propoxy) group) with ammonia ($R^{13}$=hydrogen), methylamine ($R^{13}$=methyl) or ethylamine ($R^{13}$=ethyl).

Where X is a halogen atom the reaction is a Schotten-Baumann procedure, preferably being effected in the presence of a base such as aqueous sodium hydroxide or pyridine at a temperature between −20° C. and 50° C., preferably between −5° C. and room temperature.

Where X is a hydroxyl group the reaction may be effected under standard conditions of amide formation, preferably in the presence of a suitable coupling agent, such as N,N'-carbonyldiimidazole (CDI) or dicyclohexylcarbodiimide. The reaction is conveniently effected in a solvent such as a substituted amide e.g. dimethylformamide, an ether e.g. tetrahydrofuran, or a halogenated hydrocarbon e.g. dichloromethane at a temperature between 0° and 100° C., and conveniently at room temperature.

Where X is a $C_{1-6}$alkoxy group, the reaction may be effected in the presence of an amine such as anhydrous methylamine in a sealed vessel at a temperature between room temperature and 100° C.

In the processes (A), (B), (C), (D) and (E) described above, the compounds of general formula (I) may be obtained in the form of a salt, conveniently in the form of a physiologically acceptable salt. Where desired, such salts may be converted into the corresponding free acids or free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

The intermediate compounds of general formula (II) may be prepared from a compound of formula (V):

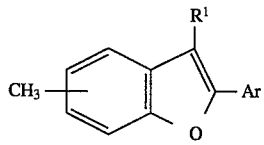

using any suitable reagent well known in the art for converting the methyl on the 6-membered ring into the group —$CH_2L$ (wherein L is as defined above). Thus, for example, when L is a halogen atom, a compound of formula (V) can be converted into a compound of general formula (II) using N-chloro amides, tert-butyl hypochlorite or N-bromosuccinimide. Halogenation of the side chain may be catalysed by light, thus the reaction can be illuminated with a suitable artificial light source, and preferably in the presence of a free radical initiator such as azobisisobutyronitrile (AIBN) or benzoyl peroxide.

Compounds of formula (V) wherein $R^1$ is a halogen atom, for example, a bromine atom, may be prepared by halogenation of a compound of formula (V) wherein $R^1$ represents a hydrogen atom, using for example, bromine, in a suitable solvent such as a halogenated hydrocarbon, e.g. carbon tetrachloride.

Compounds of formula (V) may be prepared by reaction of a compound of formula (VI)

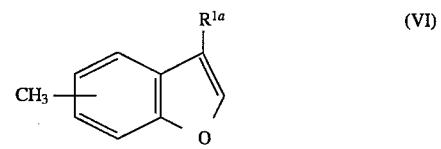

(wherein $R^{1a}$ represents a hydrogen atom or a group selected from $C_{1-6}$alkyl or $C_{2-6}$alkenyl) with a compound of formula (VII)

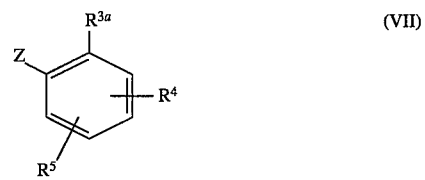

(wherein Z represents a bromine or iodine atom or a —$OSO_2CF_3$ or methoxy group, $R^4$ and $R^5$ are as defined in general formula (I) and $R^{3a}$ is as defined for $R^3$ in general formula (I) or is a protected derivative thereof).

The compound of formula (VI) is first treated with an alkyl lithium compound such as n-butyl lithium at a reduced temperature, for example, between −100° C. and 0° C. in a solvent such as an ether (e.g. tetrahydrofuran). The mixture is then treated with a trialkyl tin halide compound such as trimethyl tin chloride to produce a compound of formula (VIa). Alternatively the lithiated precursor may be treated with a tri-alkylborate compound such as triisopropylborate and the temperature conveniently brought up to room temperature. Subsequently, water may be added and the mixture treated with a mineral acid such as sulphuric acid thus producing a compound of formula (VIa)

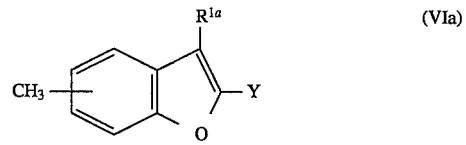

(wherein Y represents a trialkyl tin (e.g. trimethyl tin) or a boronic acid group).

The intermediate compound of formula (VIa) is then reacted with a compound of formula (VII) in the presence of a palladium (0) compound such as tetrakis(triphenylphosphine) palladium (0) in a solvent such as an ether (e.g. dimethoxyethane), and in the presence of a base such as sodium carbonate or thallium hydroxide. The reaction is conveniently effected at an elevated temperature, such as the reflux temperature of the solvent.

Compounds of formula (V) in which the substituent $R^3$ in the group Ar represents a C-linked tetrazolyl group may be prepared from a precursor of a compound of formula (V) wherein the substituent $R^3$ represents a nitrile group using the reagents and conditions described in process (C).

Similarly, intermediates of formula (VII) wherein $R^{3a}$ represents a C-linked tetrazolyl group may be prepared from a compound of formula (VIII)

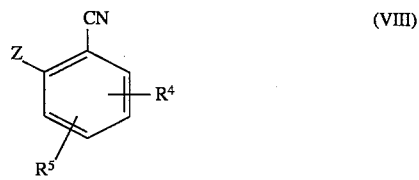

(followed where necessary by protection of any reactive groups), using methods well-known in the art such as those described in process (C).

Compounds of formula (V) in which the substituent $R^3$ in the group Ar is —$NHSO_2CF_3$ may be prepared from a precursor of a compound of formula (V) wherein the substituent $R^3$ is an amine group using the reagents and conditions described in process (D).

Similarly, intermediates of formula (VII) wherein $R^{3a}$ represents —$NHSO_2CF_3$ may be prepared from a compound of formula (IX),

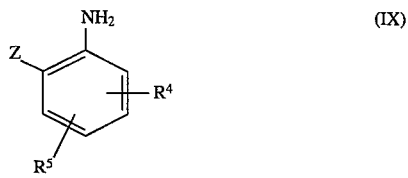

(followed where necessary by the protection of any reactive group) using methods well known in the art such as those described in process (D).

Compounds of formula (V) may also be prepared by a reaction of a compound of formula (X)

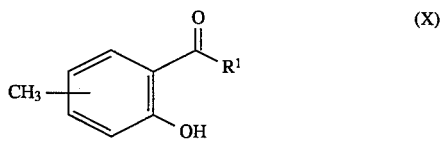

(wherein $R^1$ is as previously defined with the exception of CHO, $COR^2$, wherein $R^2$ is $C_{1-6}$alkoxy or —$NR^{10}R^{11}$, and halogen) with a suitably substituted benzene of formula (XI)

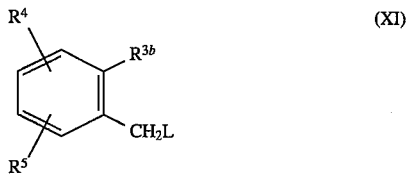

(wherein L is as previously defined and $R^{3b}$ is as defined for $R^{3a}$ in formula (VII) or is a nitrile group suitable for subsequent conversion into a tetrazolyl group or is a protected amino or nitro group suitable for conversion into —$NHSO_2CF_3$), in the presence of a base such as sodium hydride or potassium carbonate. The formation of the compound of formula (V) is a two step reaction which requires up to one equivalent of base per step. It will be appreciated however that the reaction can be effected in the presence of two equivalents of base to avoid the need to isolate the intermediate. The reaction is conveniently effected in a solvent such as an ether e.g. tetrahydrofuran, an alcohol e.g ethanol or a substituted amide e.g. dimethylformamide, at a temperature between room temperature and the reflux temperature of the solvent.

It will be appreciated that compounds of general formula (I) may be interconverted into other compounds of general formula (I). For instance, a compound wherein $R^1$ represents a halogen atom (e.g. bromine atom) may be interconverted into a compound wherein $R^1$ represents a $C_{1-6}$alkyl group (e.g. an ethyl group). The reaction is effected by the coupling of an acetylene compound (e.g. trimethylsilyl acetylene) in the presence of a palladium catalyst (such as bis(triphenylphosphine)palladium dichloride) in a suitable solvent such as a substituted amine (e.g. ethylamine) at a temperature between room temperature and the reflux temperature of the solvent. Subsequent conversion of the 3-acetylene derivative thus formed to give the required 3-alkyl substituent may be effected by conventional reduction.

Compounds in which $R^1$ represents a halogen atom (e.g. a bromine atom) may also be converted into compounds in which $R^1$ represents the group —$COR^2$ (where $R^2$ is, for example, a methoxy group) by reaction with carbon monoxide in the presence of a base such as triethylamine, palladium diacetate and 1,3-bis(diphenylphosphine)propane and a suitable alcohol (e.g. methanol). The reaction is conveniently effected in a solvent such as a substituted amide (e.g. dimethylformamide) at elevated temperature and pressure.

Compounds in which $R^8$ represents the group —$COR^{10}$ (where $R^{10}$ is a hydroxy or a $C_{1-6}$alkoxy group) may be converted into compounds in which $R^8$ represents a halogen atom (e.g. a iodine atom) by reaction with the chosen halogen in the presence of a suitable base (e.g. sodium hydroxide) and a suitable solvent such as an alcohol (e.g. methanol) or a halogenated hydrocarbon (e.g. dichloromethane). The reaction is conveniently effected at a temperature between room temperature and the reflux temperature of the solvent.

Compounds in which $R^8$ represents the group —$COR^{10}$ (where $R^{10}$ is a hydroxy group) may be decarboxylated to give a compound in which $R^8$ is a hydrogen atom by a thermal decarboxylation reaction involving heating the carboxylic acid above its melting point (e.g. between 20° and 60° above its melting point), optionally in a suitable high boiling solvent (e.g. 2,4,6-collidine).

It will be appreciated that apart from the interconversion of one compound of general formula (I) into another, these reactions may also be used in the preparation of suitable intermediates. Other reactions of intermediates include, for instance, the conversion of compounds of formula (V) in which $R^1$ represents a hydrogen or halogen atom into compounds of formula (V) in which $R^1$ represents the group methyl (via hydrogenolysis of the Mannich base), —CHO or —$COR^2$ (wherein $R^2$ is as defined in general formula (I)) using techniques well known in the art, such as those described in "Heterocyclic Chemistry" by J. A. Joule and G. F. Smith, Van Nostrand Reinhold Company, London (1972), "Heterocyclic Chemistry" by A. Albert, 2nd Edition, The Athlone Press, London (1968), "Heterocyclic Compounds", Vol. 29 by A. Mustafa, John Wiley and Sons Inc., New York (1974), "Heterocyclic Compounds", Vol. 2 by R. C. Elderfield, John Wiley and Sons Inc., New York (1951) and "Advances in Heterocyclic Chemistry", Vol. 29 by A. R. Katritsky and A. J. Boulton, Academic Press, New York (1981).

The imidazoles of formula (III) may be prepared as described in European Specification No. 0253310A and in U.S. Pat. No. 4,355,040 or by methods analogous to those described therein. The content of these references is hereby incorporated by reference.

Imidazoles of general formula (IIIa) wherein L' represents a bromine atom may be prepared from an imidazole of general formula (XII)

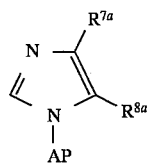

by metallation, followed by bromination, of the imidazole 2-position. Metallation may be effected by treatment with an alkyl lithium compound such as n-butyl lithium, whilst bromination may be effected by treatment with N-bromosuccinimide. In general formula (XII) AP represents a suitable nitrogen protecting group whilst $R^{7a}$ and $R^{8a}$ represent substituent groups that are unaffected by the metallation and bromination-reactions, but may, subsequently be converted to the groups $R^7$ and $R^8$, if necessary.

Intermediates of formulae (VI), (VII), (VIII) (IX), (X), (XI) and (XIII) are either known compounds or may be prepared by methods analogous to those used for the preparation of the known compounds.

The following examples illustrate the invention. Temperatures are in °C. "Dried" refers to drying using magnesium sulphate. Thin layer chromatography (T.l.c.) was carried out on silica and column chromatography was carried out on silica (Merck 9385 unless otherwise stated), using one of the following solvent systems: A—ether:hexane, B—ether:dichloromethane, C— dichloromethane:ethanol:conc. aqueous ammonia, D— dichloromethane:ethyl acetate, E—dichloromethane:ether:acetic acid, F—dichloromethane:methanol, G—dichloromethane:methanol:acetic acid, H—ethyl acetate:acetic acid, I—ether:ethyl acetate or J—ethyl acetate:hexane.

Proton n.m.r. spectra were measured on a Bruker WM250 (250 MHz) spectrometer.

The following abbreviations are used: THF—tetrahydrofuran; DME—dimethoxyethane; AIBN—azobisisobutyronitrile; DMF— dimethylformamide; TMEDA—tetramethylethylenediamine; NBS—N-bromosuccinimide; DMAP—4-dimethylaminopyridine; DEAD—diethyl azodicarboxylate; DMSO—dimethylsulphoxide.

The following abbreviations are used in the Tables of exemplification: Et=ethyl; Pr=propyl; Bu=butyl; Hex=hexyl; c-Pr=cyclopropyl; c-Bu=cyclobutyl; c-Hex=cyclohexyl; Ph= phenyl; Py=2-pyridinyl; Tet-P=2-(triphenylmethyl)-2H-tetrazole; t-BOC=N-tert-butoxycarbonyl.

INTERMEDIATE 1

5-Methylbenzofuran-2-boronic Acid n-Butyl lithium (35.16 ml) was added dropwise to a stirred solution of TMEDA (9.58 ml) and 5-methylbenzofuran (8.22 g) in ether (250 ml) maintaining the temperature below −60° C. throughout. The solution was warmed to about −10° C. over 45 minutes and stirred at this temperature for 30 minutes. A precipitate formed on warming. The suspension was cooled and triisopropylborate (43 ml) was added, maintaining the temperature below −60° C. The solution was warmed gradually to room temperature before quenching with 2N HCl (70 ml). The mixture was extracted with ether (3×50 ml) and the combined organic extracts washed with 2N HCl (4×30 ml), water (2×30 ml) and dried before evaporation to give the title compound as an orange solid (12.75 g).

T.l.c. System A (1:1), Rf 0.3.

INTERMEDIATE 2

Methyl 2-(5-methyl-2-benzofuranyl)benzoate

A solution of methyl 2-bromobenzoate (11.70 g), Intermediate 1 (12.75 g) and tetrakistriphenylphosphine palladium (0) (0.5 g) in DME (300 ml) and 2N aqueous $Na_2CO_3$ (60 ml) was heated at reflux with vigorous stirring under nitrogen. After 1.5 h a further 500 mg of catalyst was added and stirring at reflux under nitrogen continued. After about 5 h the reaction was cooled to room temperature and diluted with ether (300 ml). The organic layer was separated and washed with water (3×100 ml) and dried. Filtration and evaporation gave a yellow oily suspension (19.27 g) which was purified by chromatography eluting with System A (1:9) to give a yellow oil (11.06 g). This was further purified by Kugelrohr distillation to give the title compound (4.31 g).

T.l.c. System A (1:9), Rf 0.5.

INTERMEDIATE 3

Methyl 2-(3-bromo-5-methyl-2-benzofuranyl)benzoate

A solution of Intermediate 2 (0.25 g) in carbon tetrachloride (5 ml) was cooled to −20° C. and treated dropwise with 1M bromine in carbon tetrachloride (0.7 ml). Stirring at −20° C. was then continued for 1 h before gradual warming to room temperature. Stirring at room temperature was continued overnight. Cyclohexene (0.1 ml) was added dropwise and the solvents were evaporated in vacuo to give the title compound as an orange oil (0.26 g).

T.l.c. System A (1:9), Rf 0.45.

INTERMEDIATE 4

2-(3-Bromo-5-methyl-2-benzofuranyl)benzoic Acid

A solution of Intermediate 3 (2.20 g) in methanol (20 ml) was treated with aqueous sodium hydroxide (2N;3 ml). The solution was heated to reflux and heating was continued for 3 h. The solvent was removed in vacuo and the residue diluted with water. The basic aqueous phase was washed with ether (3×30 ml) before acidification to pH~2 using 2N HCl. A white suspension formed. This was extracted with ether (4×20 ml) and these combined organic extracts dried and evaporated to give the title compound as a pale yellow solid (1.93 g).

T.l.c. ether, Rf 0.7

INTERMEDIATE 5

1,1-Dimethylethyl[2-(3-bromo-5-methyl-2-benzofuranyl)phenyl]carbamate

A solution of Intermediate 4 (1 g) in dry dioxan (25 ml) was treated with diphenylphosphorylazide (0.65 ml), triethylamine (0.42 ml) and tert-butanol (0.5 ml) before heating to reflux under nitrogen. After 6 h the reaction was cooled and solvent evaporated to give an orange oil. Purification by column chromatography, eluting with System A (1:10) afforded the title compound as a cream solid (0.67 g).

T.l.c. System A (1:1), Rf 0.8

INTERMEDIATE 6

1,1-Dimethylethyl [2-[3-bromo-5-(bromomethyl)-2-benzofuranyl] phenyl]carbamate A solution of Intermediate 5 (4.29 g), NBS (2.9 g) and benzoyl peroxide (30 mg) in dry carbon tetrachloride (100 ml) was heated at reflux whilst being irradiated with a 200 W lamp for 1.5 hours. The mixture was filtered, and the filtrate was washed with water (2× 100 ml). The organic solution was dried, filtered and evaporated to give the title compound (5 g).

T.l.c. System A (1:1) Rf 0.73.

INTERMEDIATE 7

2-(5-Methyl-2-benzofuranyl)benzonitrile

Intermediate 1 (20 g) was added to a stirred solution of 2-bromobenzonitrile (10.34 g) and tetrakistriphenylphosphine palladium (0) (1.5 g) in DME (200 ml) and 8% aqueous NaHCO$_3$ (50 ml) at reflux under nitrogen. Further catalyst (1.5 g) was added and the reaction was heated overnight. The reaction was cooled to room temperature and diluted with ether (200 ml). The organic layer was separated, washed with water (3×100 ml) and dried. Filtration and evaporation gave a white solid which was purified by chromatography eluting with System A (1:9) to give the title compound (10.58 g) as a white solid.

T.l.c. System A (1:9), Rf 0.45.

Intermediate 7 was also prepared by an alternative two-step reaction:

a) 2-Hydroxy-5-methylbenzaldehyde p-Cresol (100 g) in dry THF (100 ml) was added over 30 minutes dropwise to a mechanically stirred, freshly prepared solution of ethyl magnesium bromide [magnesium (25.0 g) and bromoethane (75 ml)] in THF (500 ml) under nitrogen at a rate which maintained a slow reflux. After a further 30 mins toluene (1.21) was added, followed by 1,3-dimethyl-3,4,5,6-tetrahydro-2(1H)-pyrimidone (125 ml), and paraformaldehyde (70 g). The mixture was then heated at reflux for 16 h. The mixture was concentrated by distillation and aqueous hydrochloric acid (2M, 600 ml) then added. Water (600 ml) was added and the mixture filtered through "hyflo", dried and concentrated in vacuo to give a brown oil. The oil was steam distilled and the product extracted from the distillate with ether (1 liter). The organic extract was dried and concentrated in vacuo to give a pale yellow slurry which was triturated with ether at −10° C. to give the title compound as colourless needles, (131.4 g).

T.l.c. System A (1:5) Rf 0.5.

b) 2-(5-Methyl-2-benzofuranyl)benzonitrile

A solution of the product of step (a) (130 g) in dry DMF (400 ml) was added dropwise to a solution of sodium methoxide (56.2 g) in ethanol (400 ml) mechanically stirred under nitrogen. After a further 20 mins, a solution of 2-(bromomethyl)benzonitrile (182.2 g) in dry DMF (400 ml) was added dropwise. The mixture was then heated to 75° C. for 30min. The solution was allowed to cool for 1 h. A slurry of sodium methoxide (56.2 g) in dry DMF (100 ml) was added and the mixture heated at reflux for 1.5 h. The mixture was concentrated in vacuo and then poured into iced water. The solid was collected, and then triturated with methanol to give the title compound (Intermediate 7) as a beige solid (149.4 g).

T.l.c. System A (1:9) Rf 0.4.

INTERMEDIATE 8

5-[2-(5-Methyl-2-benzofuranyl)phenyl]-1H-tetrazole

A suspension of Intermediate 7 (94 g) in tri-n-butyl tin azide (268 g) was heated at 100°–125° C. for 1.25 h under nitrogen. The resulting solution was then heated at 155°–160° C. for 2 h under nitrogen, then poured into a solution of aqueous sodium hydroxide (0.8N, 3070 ml). This solution was extracted with ether. The aqueous phase was acidified to pH1 with 5N hydrochloric acid and the resulting precipitate filtered, washed with water and dried under vacuum. The solid was dissolved in ethyl acetate, and the solution was washed with brine and dried. The solvent was evaporated to give the title compound as a buff-coloured solid (100.3 g).

T.l.c. System A (1:1), Rf 0.2.

INTERMEDIATE 9

5-[2-(3-Bromo-5-methyl-2-benzofuranyl)phenyl]-1H-tetrazole

A solution of bromine (58 g), in carbon tetrachloride (140 ml) was added dropwise over 35 min to a mechanically stirred solution of Intermediate 8 (50 g) in dry dioxan (2090 ml) at room temperature under nitrogen. The resulting solution was stirred at room temperature for 3 h, then cyclohexene (63 ml) was added. Another preparation of the product was carried out simultaneously on the same scale as described above, and at this stage they were combined. The solvent was evaporated and the residual brown oil (260 g) partitioned between ether and aqueous 2M sodium hydroxide. The alkaline solution was acidified to pH1 with hydrochloric acid, then extracted with ethyl acetate. The combined ethyl acetate extracts were washed with brine, dried and evaporated to give a buff solid (125 g) which was triturated under hot toluene to give the title compound as a cream coloured solid (101.8 g).

T.l.c. ether/petroleum ether/acetic acid (50:50:1), Rf 0.27.

INTERMEDIATE 10

5-[2-(3-Bromo-5-methyl-2-benzofuranyl)phenyl]-2-(triphenylmethyl)- 2H-tetrazole Triethylamine (57.4 g) was added to a mechanically stirred suspension of Intermediate 9 (101 g) in dry dichloromethane (2.9 liters) at room temperature under nitrogen. Triphenylmethyl chloride (79.3 g) followed by DMAP (1.0 g) were added at room temperature and the mixture stirred for 3 h under nitrogen. The reaction mixture was washed with water, then brine and dried. The solvent was filtered and concentrated to a volume of about 1.2 liters then filtered through silica (Merck 9385, 14cm diam. column). Elution with dichloromethane gave a colourless solid (158.4 g) which was triturated with ether to give the title compound as a colourless solid (147.9 g).

T.l.c. (Dichloromethane/hexane 1:1), Rf 0.28

INTERMEDIATE 11

5-[2-[3-Bromo-5-(bromomethyl)-2-benzofuranyl]phenyl]-2-(triphenylmethyl)-2H-tetrazole Intermediate 10 (74 g) was dissolved in carbon tetrachloride (2050 ml) by heating the suspension to reflux. The resulting colourless solution was allowed to cool to 50° C.

then NBS (22.1 g) was added, followed by benzoyl peroxide (1.1 g). The reaction mixture was heated at reflux for 3.25 h, under nitrogen, then allowed to cool to room temperature. The reaction mixture was washed with water then brine. Another preparation of the product was carried out simultaneously on the same scale as described above, and at this stage they were combined and dried. The solvent was evaporated to give a colourless solid (168 g) which was triturated with ether/methanol (1:1) and filtered to give the title compound as a colourless solid (160.8 g).

T.l.c. (Dichloromethane/hexane 1:1), Rf 0.15.

INTERMEDIATE 12

Ethyl α-amino-62 -oxocyclopropanepropanoate Hydrochloride

Acetyl chloride (15.35 ml, 16.88 g) was added to a cooled solution of ethyl α-(hydroxyimino)-β-oxocyclopropanepropanoate (20 g) in absolute ethanol (250 ml) before being added to a suspension of 5% platinum on carbon (1.85 g) in absolute ethanol (150 ml). The stirred mixture was then hydrogenated at room temperature and pressure for 5 h. The catalyst was filtered off through a pad of hyflo and the filtrate concentrated in vacuo to give, after azeotroping with toluene (2× 80 ml), an off-white solid. This was triturated with ether (500 ml) to give the title compound (14.5 g) as a white solid. m.p. 196–197° C.

Intermediate 12 was also prepared by an alternative two-step reaction:

(a) Ethyl 5-cyclopropyl-4-oxazolecarboxylate

A mixture of ethyl isocyanoacetate (13.4 g) in THF (65 ml) was added dropwise to a stirred solution of potassium tert-butoxide (14.5 g) in THF (97 ml) at 0° C. Cyclopropanecarboxylic acid chloride (5.4 ml) was added dropwise at below 10° C. and the solvent evaporated. Water (68 ml) and acetic acid (3.4 ml) was added to the mixture, then diisopropyl ether (2×150 ml) was added and the layers separated. The aqueous layer was further extracted with diisopropyl ether (2× 150 ml) and the combined organic extracts were dried. Evaporation of the solvent afforded the title compound as a yellow oil (8.3 g).

n.m.r. (CDCl₃) δ 1.03 (4H,m), 1.34 (3H,t), 2.70 (1H,m), 4.32 (2H,q), 7.53 (1H,d).

(b) Ethyl α-amino-β-oxocyclopropanepropanoate Hydrochloride

Concentrated hydrochloric acid (21.5 ml) was added to a solution of the product of step (a) (9.3 g) in ethanol (65 ml). The mixture was heated at 50° C. for 1 h, cooled and the solvent was evaporated. Toluene (3×50 ml) was added to the residue and was evaporated after each addition. The residue was triturated with diisopropyl ether (80 ml) to give the title compound (Intermediate 12) as a pale brown powder (6.8 g) m.p. 158°–159° C.

INTERMEDIATE 13

Ethyl 4-cyclopropyl-2-ethyl-1H-imidazole-5-carboxylate

A solution of Intermediate 12 (14.5 g) in absolute ethanol (110 ml) was added dropwise over 1 h to a stirred suspension of ethyl propanimidate hydrochloride (25.1 g) and triethylamine (32 ml, 22.7 g) in absolute ethanol (200 ml). After stirring overnight under nitrogen, the grey suspension was concentrated in vacuo to afford a grey residue which was partitioned between ethyl acetate (250 ml), ethanol (50 ml), water (200 ml) and saturated sodium chloride (100 ml). The aqueous phase was further extracted with ethyl acetate (2× 100 ml) and the combined organic extracts were dried and concentrated in vacuo to afford a grey solid (31 g). Purification by chromatography eluting with System A (1:3) increasing to (1:1) gave the title compound (3.5 g) as a white solid. m.p. 154°–155° C.

INTERMEDIATE 14

4-Methyl-1-(triphenylmethyl)-1H-imidazole

A suspension of triphenylmethyl chloride in anhydrous DMF (100 ml) was slowly added to a stirred solution of 4-methylimidazole (12.30 g) and triethylamine (41.8 ml) in anhydrous DMF (200 ml). After stirring the resultant slurry for ca. 3 h it was added to water (750 ml) and the solid removed by filtration. The solid was dissolved in dichloromethane (500 ml) and residual water separated. The organic solution was dried and evaporated to dryness to give the title compound as a white solid (42.7 g).

T.l.c. System C (100:8:1) Rf=0.71.

INTERMEDIATE 15

2-Bromo-4-methyl-1-(triphenylmethyl)-1H-imidazole

A solution of n-butyllithium in hexane (1.55M; 95 ml) was added to a stirred solution of Intermediate 14 (40.0 g) in freshly distilled THF (2500 ml) and DME (500 ml) at 5° C. under nitrogen, The resulting light orange suspension was stirred at 20° C. for 1 h before cooling to 5° C. and dropwise addition of NBS (21.9 g) in freshly distilled THF (100 ml) to give a buff suspension. After stirring overnight at room temperature water (100 ml) was added and the resulting solution concentrated to ca 1000 ml. Further water (1500 ml) was added and the mixture extracted with dichloromethane (3'500 ml). The combined extracts were washed with saturated brine (500 ml) dried and concentrated in Vacuo to give a brown solid. Flash column chromatography eluting with 5% ether in dichloromethane gave the title compound as a white solid (24.0 g).

T.l.c. ether:petroleum ether (1:1) Rf=0.50.

INTERMEDIATE 16

2-Bromo-4(5)-methyl-1H-imidazole

A suspension of the Intermediate 15 (23.8 g) in 5% acetic acid in methanol (250 ml) and freshly distilled THF (50 ml) was heated at reflux for ca 2.5 h. to give a yellow solution, The mixture was evaporated to dryness to give a yellow/white solid to which water (250 ml) was added. The resulting suspension was vigorously stirred for ca 30 min before filtration and thorough washing of the solid with water. The combined filtrate and washings were concentrated in vacuo to give the title compound as a light yellow powder (8.20 g).

T.l.c. System A (1:1) Rf=0.18.

INTERMEDIATE 17

2-Bromo-4-methyl-1H-imidazole-5-methanol

37% Aqueous formaldehyde (3.1 ml) was added to a solution of Intermediate 16 (4.00 g) in water (25 ml) and ethanol (50 ml) and 2N aqueous sodium hydroxide (12.5 ml). After standing overnight the solution was acidified to ca pH8 with 2N hydrochloric acid and concentrated to a small volume (ca 10 ml), Saturated brine (100 ml) was added and the mixture extracted with (4:1) chloroform/ispropanol (3×75 ml). The combined extracts were dried and concentrated in vacuo to give a yellow wax. Trituration with ether gave the title compound as a buff powder (3.70 g).

T.l.c. ether Rf=0.13

INTERMEDIATE 18

2-Bromo-4-methyl-1H-imidazole-5-carboxaldehyde

Manganese dioxide (7.40 g) was added to a stirred solution of Intermediate 17 (1.90 g) in (1:1) dichloromethane/ 1,4-dioxan (100 ml) and the resulting suspension heated at reflux under nitrogen overnight. The suspension was filtered through hyflo and the filtrate concentrated in vacuo to give a yellow solid. Trituration with System A (1:1) gave the title compound as a light yellow powder (1.20 g).

T.l.c. ether Rf=0.58.

INTERMEDIATE 19

Ethyl 1-[[3-bromo-2-[2-[2-(triphenylmethyl)-2H-tetrazol-5-yl] phenyl]-5-benzofuranyl]methyl]-4-cyclopropyl-2-ethyl-1H-imidazole- 5-carboxylate A mixture of Intermediate 13 (1.67 g), Intermediate 11 (6.76 g), and potassium carbonate (1.33 g) in dry DMF (20 ml) was stirred at room temperature for 18 h. The mixture was partitioned between ethyl acetate (3×100 ml) and brine/ water 1:1 (150 ml). The combined organic extracts were washed with brine/water 1:1 (3×150 ml) and dried. The solvent was evaporated to give a pale yellow gum (7 g) which was purified by flash column chromatography eluting with System A (1:1) to give the title compound as a colourless foam (4.32 g).

T.l.c. System A (1:1) Rf 0.3.

Similarly prepared was:

INTERMEDIATE 20

Ethyl 1-[[3-bromo-2-[2-[[1,1-dimethylethoxy)carbonyl]amino]phenyl]-5-benzofuranyl]methyl]-4-cyclopropyl-2-ethyl-1H-imidazole-5-carboxylate n.m.r. (CDCl$_3$) δ 0.8–1.0(4H,m), 1.23(3H,t), 1.32(3H,t), 1.5(9H,s), 2.58–2.72(3H,m), 4.28(2H,q), 5.65(2H,s), 7.01(1H,dd), 7.1–7.2(2H,m), 7.4–7.5(2H,m), 7.63(1H,dd), 8.17(1H,d).

From Intermediate 13 and Intermediate 6.

INTERMEDIATE 21

1-[[3-Bromo-2-[2-[2-(triphenylmethyl)-2H-tetrazol-5-yl]phenyl]-5benzofuranyl] methyl]-2-cyclopropyl-4-methyl-1H-imidazole-5-carboxaldehyde Intermediate 11 (1.81 g) was added to a stirred mixture of 2-cyclopropyl- 4-methyl-1H-imidazole-5-carboxaldehyde (350 mg) and potassium carbonate (320 mg) in anhydrous DMF. The resulting suspension was stirred for ca. 36 h at room temperature to afford a yellow solution. Water (50 ml) was added and the mixture extracted with dichloromethane (3×50 ml). The combined extracts were washed with water (3×50 ml) dried and concentrated in vacuo to give a brown oil. Flash column chromatography eluting with ether gave the title compound as a white foam (1.00 g).

T.l.c. ether Rf=0.42.

Similarly prepared was:

INTERMEDIATE 22

2-Bromo-1-[[3-bromo-2-[2-[2-(triphenylmethyl)-2H-tetrazol-5-yl ]phenyl]-5-benzofuranyl]methyl]-4-methyl-1H-imidazole-5-carboxaldehyde T.l.c. ether:hexane:dichloromethane (10:30:100) Rf=0.53.

From Intermediate 11 (3.70 g) and Intermediate 18 (900 mg). Purification by column chromatography eluting with ether:hexane:dichloromethane (10:100:100) gave the title compound as a white foam (1.70 g).

INTERMEDIATE 23

Ethyl 1-[[2-(2-aminophenyl)-3-bromo-5-benzofuranyl]methyl]-4-cyclopropyl-2-ethyl-1H-imidazole-5-carboxylate Trifluoroacetic acid (5 ml) was added to a stirred solution of Intermediate 20 (2.55 g) in dichloromethane (40 ml) at 30 under 30 nitrogen. After allowing to warm to room temperature and stirring for 4 h. the solution was cautiously neutralised with 8% sodium bicarbonate (50 ml), was washed with 8% aqueous sodium bicarbonate (40 ml), dried and concentrated in vacuo to afford a dark yellow viscous oil (2.15 g). Purification by chromatography eluting with ether afforded the title compound (2.0 g) as a white foam.

n.m.r. (CDCl$_3$) δ 0.9–1.1(m,4H), 1.21(t,3H), 1.31(t,3H), 2.58– 2.62(m,3H), 4.24–4.34(m,4H), 5.62(s,2H), 6.77–7.0(m,3H), 7.2– 7.3(m, 2H), 7.42(d, 1H), 7.6(dd, 1H).

Intermediate 23 was also prepared by an alternative method:

INTERMEDIATE 23 (ALTERNATIVE METHOD)

Ethyl 1-[[2-(2-aminophenyl)-3-bromo-5-benzofuranyl]methyl]-4-cyclopropyl-2-ethyl-1H-imidazole-5-carboxylate Iron powder (17 g) was added to a stirred solution of Intermediate 74 (40 g) in ethanol (450 ml), water (140 ml) and acetic acid (140 ml) and the mixture heated at reflux for 1.5 h. The mixture was cooled, filtered ("celite") and washed with ethanol (2×300 ml). The combined filtrate and washings were evaporated to a thick slurry, water (1 liter) was added and the pH adjusted to 9–10 by the addition of solid sodium carbonate. Water (1 liter) and ethyl acetate (1 liter) were added, the mixture filtered ("celite") and the organic-layer was separated. The aqueous layer was further extracted with ethyl acetate (750 ml and 250 ml). The combined organic extracts were washed with brine (300 ml) and evaporated to a solid which was recrystallised from diisopropyl ether (150 ml) to give the title compound as an off-white solid (27.9 g).

Assay Found: C,61.5; H,5.3; N,8.2; Br, 15.8;

$C_{26}H_{26}BrN_3O_3$ requires: C,61.4; H,5.15; N,8.3; Br, 15.7%

INTERMEDIATE 24

1-[[3-Bromo-2-[2-[2-(triphenylmethyl)-2H-tetrazol-
5-yl]phenyl]-
5-benzofuranyl]methyl]-2-cyclopropyl-4-methyl-
1H-imidazole-5-carboxylic Acid A solution of 80% sodium chlorite (1.13 g) and sodium dihydrogenorthophosphate dihydrate (1.13 g), in water (20 ml) was added dropwise to a stirred solution of Intermediate 21 (950 mg) in freshly distilled THF (20 ml), t-butanol (20 ml) and 2-methylbut-2-ene (0.59 ml). The mixture was rapidly stirred at room temperature for 48 h before concentration to ca 25 ml and addition of water (100 ml). The mixture was extracted with ethyl acetate (3×100 ml) and the combined extracts dried and concentrated in vacuo to give a white foam. Flash column chromatography eluting with 5% acetic acid/5% dichloromethane in ether gave the title compound as a white foam (700 mg).

T.l.c. 5% acetic acid in ether Rf=0.18

INTERMEDIATE 25

1-[[3-Bromo-2-[2-[2-(triphenylmethyl)-2H-tetrazol-
5-yl]phenyl]-
5-benzofuranyl]methyl]-2-ethoxy-4-methyl-
1H-imidazole-5-carboxaldehyde A solution of Intermediate 22 (1.00 g) and sodium ethoxide (0.43 g) in (1:1) ethanol/THF (25 ml) was heated at reflux overnight. The solution was concentrated to a small volume (ca 5 ml), water (100 ml) added and the mixture extracted with dichloromethane (3×75 ml). The combined extracts were dried and concentrated in vacuo. Flash column chromatography eluting with ether:dichloromethane (2:1) gave the title compound as a yellow foam (400 mg).

T.l.c. ether Rf=0.37.

INTERMEDIATE 26

1-[[3-Bromo-2-[2-[2-(trifluoromethyl)sulphonyl]
amino]phenyl]-5-benzofuranyl]
methyl]-4-cyclopropyl-2-ethyl-1H-imidazol-5-yl]
carbonyl]-1H-imidazole 1,1-Carbonyldiimidazole (0.73 g) was added to a solution of the product of Example 5 (1.7 g) in THF (100 ml). The resulting suspension was then stirred at room temperature for 60 h, filtered and the filtrate was concentrated in vacuo to afford the title compound (1.9 g) as a white foam.

T.l.c. System F (15:1), Rf 0.65(Streak).

INTERMEDIATE 27

1,1-Dimethylethyl
2-(3-bromo-5-methyl-2-benzofuranyl)benzoate

The title compound was prepared from Intermediate 1 and 1,1-dimethylethyl 2-bromobenzoate according to the method of Intermediate 2, followed by bromination according to the method of Intermediate 3.

T.l.c. dichloromethane:hexane (1:2) Rf=0.3

INTERMEDIATE 28

1,1-Dimethylethyl
2-[3-bromo-5-(bromomethyl)-2-benzofuranyl]benzoate

The title compound was prepared from Intermediate 27 according to the method of Intermediate 6.

T.l.c. System A (1:10) Rf=0.4

Intermediates 29 to 36 in Table 1a were prepared according to the method of Intermediate 19 from Intermediate 6, 11 or 28 and the corresponding imidazole intermediate (Equation 1a):

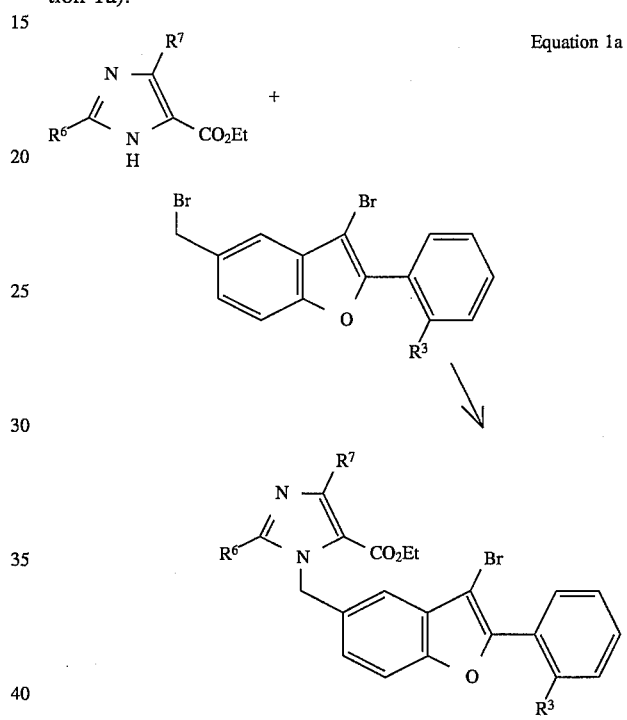

Equation 1a

Intermediates 37 to 39 in Table 1b were prepared according to the method of Intermediate 23 (Equation 11b):

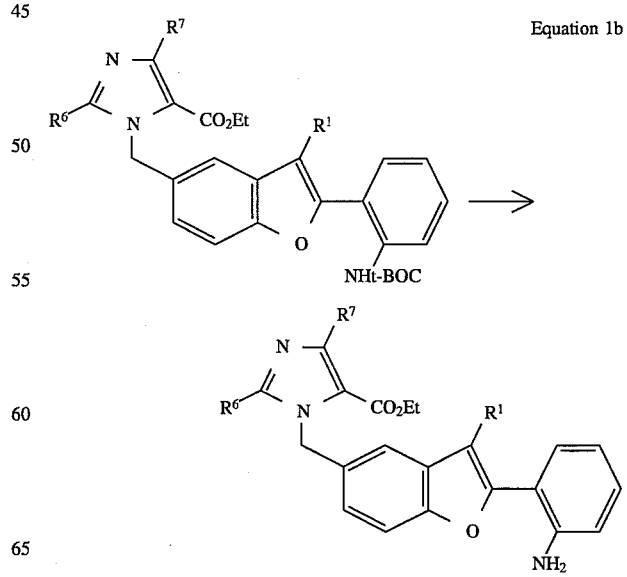

Equation 1b

INTERMEDIATE 40

Ethyl
4-cyclopropyl-1-[[2-[2-[[(1,1-dimethylethoxy)carbonyl]
amino]phenyl]-3-[(trimethylsilyl)ethynyl]-5-
benzofuranyl]methyl]-2-ethyl-
1H-imidazole-5-carboxylate Trimethylsilylacetylene (8 ml) then bis(triphenylphosphine)palladium dichloride (0.86 g) and copper (I) iodide (0.26 g) were added to a solution of Intermediate 20 (7.05 g) in diethylamine (40 ml). The contents were heated (90° C.) in a sealed vessel for 29 h. After cooling, the residue was diluted with ethyl acetate (300 ml) and washed with water (300 ml). The dried organic extract was concentrated in vacuo and the residue purified by flash chromatography eluting with System A (1:3) to give title compound as a yellow foam (2.4 g).

T.l.c. System A (2:3) Rf=0.4

INTERMEDIATE 41

Ethyl
4-cyclopropyl-1-[[2-[2-[[(1,1-dimethylethoxy)carbonyl]
amino]phenyl]-3-ethynyl-5-benzofuranyl]methyl]-
2-ethyl-1H-imidazole- 5-carboxylate 2M Aqueous sodium hydroxide (60 ml) was added to a stirred solution of Intermediate 40 (2.38 g) in methanol (40 ml)/THF (15 ml) and stirring continued for 16 h at ambient temperature. The resulting mixture was concentrated in vacuo and partitioned between dilute hydrochloric acid (pH4) and ethyl acetate. The dried organic extract was concentrated in vacuo and the residue purified by flash chromatography eluting with System A (3:7) to give the title compound as a yellow foam (1.51 g).

T.l.c. System A (2:1) Rf=0.5

INTERMEDIATE 42

Ethyl
4-cyclopropyl-1-[[2-[2-[[(1,1-dimethylethoxy)carbonyl]
amino]phenyl]-3-ethyl-5-benzofuranyl]methyl]-2-ethyl-
1H-imidazole-5-carboxylate A solution of Intermediate 41 (600 mg) in ethanol (35 ml) containing 10% palladium on carbon (300 mg) was hydrogenated at room temperature and pressure for 17 min. The separated organic solution was concentrated in vacuo to give the title compound as a white foam (530 mg).

T.l.c. System A (2:1) Rf=0.45

INTERMEDIATE 43

Trimethyl (5-methyl-2-benzofuranyl)stannane n-Butyl lithium (1.57M in hexane, 75 ml) was added dropwise to a stirred solution of 5-methylbenzofuran (14 g) in dry THF (150 ml) at −70° under nitrogen over 45 min. The solution was then allowed to warm to −55° before a solution of trimethyltin chloride (23 g) in THF (70 ml) was added dropwise. The solution temperature rose to −32°. The cooling bath was removed and the solution was stirred at room temperature for 2 h. The solution was diluted with ethyl acetate (250 ml) and washed with water (200 ml). The organic layer was dried and concentrated in vacuo to afford a yellow liquid (32 g). Kugelrohr distillation of this liquid gave the title compound (23.3 g) as a colourless liquid, b.p. 115° at 7 mbar.

INTERMEDIATE 44

Methyl 2-fluoro-6-iodobenzoate

Concentrated sulphuric acid (0.5 ml) was added to a solution of 2-fluoro- 6-iodobenzoic acid (1.03 g) in methanol (35 ml). After stirring at reflux for 5 days, with two further amounts of conc. sulphuric acid (1 ml) being added after 1 and 2 days, the solution was allowed to cool. The reaction mixture was diluted with ethyl acetate (200 ml) before being washed with water (2×80 ml), 8% aqueous sodium bicarbonate (2×100 ml), dried and concentrated in vacuo. Purification by chromatography eluting with System A (1:3) afforded the title compound (0.72 g) as an orange oil.

T.l.c. System A (1:1) Rf 0.6

INTERMEDIATE 45

Methyl 2-fluoro-6-(5-methyl-2-benzofuranyl)benzoate

Tetrakis(triphenylphosphine)palladium (0) (0.19 g) was added to a stirred solution of Intermediate 43 (1.2 g) and Intermediate 44 (0.95 g) in toluene (30 ml). The solution was then stirred at reflux for 3 h before being cooled, diluted with ethyl acetate (35 ml), washed with water (1×50 ml), dried and concentrated in vacuo to afford a red oil (1.7 g). Purification by chromatography (Merck 7734) eluting with System A (1:9) afforded the title compound (0.83 g) as a yellow oil.

Assay Found: C,71.9; H,4.35;

$C_{17}H_{13}FO_3$ requires: C,71.8; H,4.6%

Intermediates 46 to 48 in Table 2a were prepared according to the method of Intermediate 45 from Intermediate 43 and the appropriate benzoic acid ester (Equation 2a):

Equation 2a

Intermediates 49 to 52 in Table 2b were prepared by treatment of Intermediates 45 to 48, respectively, either with bromine in carbon tetrachloride followed by NBS in the presence of benzoyl peroxide as described in Intermediates 9 and 11, to give Intermediates 49 and 52, or with just NBS in the presence of benzoyl peroxide as described in Intermediate 11 to give Intermediates 50 and 51 (Equation 2b):

Equation 2b

-continued

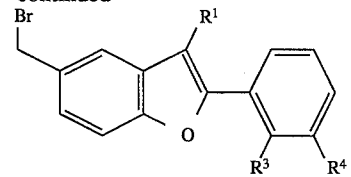

Intermediates 53 to 56 and Example 67 in Table 2c were prepared according to the method of Intermediate 19 by reaction of Intermediates 49 to 52, respectively, with the corresponding imidazole intermediate (Equation 2c):

Equation 2c

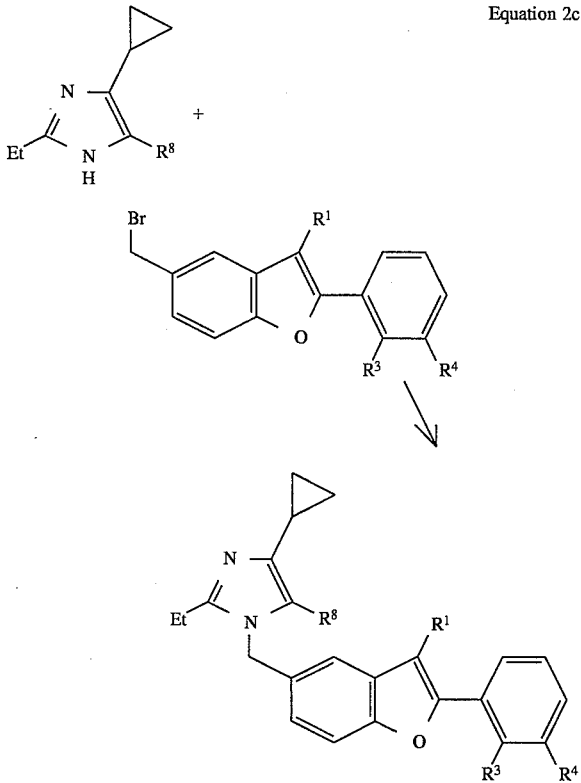

The intermediate imidazoles utilised in these examples may be prepared as follows. Intermediates 57 to 61 in Table 10 were prepared according to the method of Intermediate 13 (Equation 10):

Equation 10

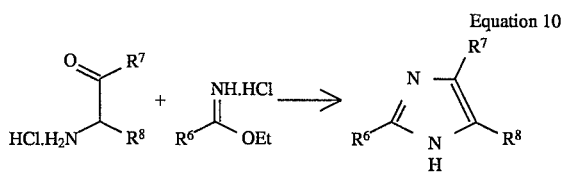

INTERMEDIATE 62

Ethyl 2-cyclobutylmethyl-4-(trifluoromethyl)-1H-imidazole-5-carboxylate

A suspension of Intermediate 61 (1.25 g) and 4 Å sieves (1.2 g) in toluene (40 ml) was refluxed for 60 h. The reaction was filtered, washed in with dichloromethane and evaporated to give the title compound as an off-white solid (1.15 g), m.p. 136°–138° C.

INTERMEDIATE 63

4-Cyclopropyl-2-ethyl-1H-imidazole-5-carboxylic Acid

A mixture of Intermediate 13 (2 g), sodium hydroxide (2N; 35 ml) and methanol (40 ml) was heated at reflux for 2×2 h before being evaporated. It was then cooled to 0°–5° C. and hydrochloric acid (35 ml) added with stirring. The resulting precipitate was filtered and dried to give the title compound as a white solid (1.4 g), m.p. 206° C. (decomp.)

INTERMEDIATE 64

1,1-Dimethylethyl 4-cyclopropyl-2-ethyl-1H-imidazole-5-carboxylate

A suspension of Intermediate 63 (1 g) in toluene (10 ml) at 80° C. was treated with dimethylformamide di-tert-butyl acetal (4.1 g) dropwise over a 5 min period. The mixture was cooled and diluted with toluene (50 ml). The organic solution was washed with water (50 ml), aqueous sodium carbonate (2M; 50 ml) and aqueous lithium chloride (10% w/v; 50 ml), dried and evaporated in vacuo to give the title compound as a pink solid (0.57 g).

T.l.c. System F (10:1) Rf 0.4

INTERMEDIATE 65

2-(Cyclopropylmethyl)-1H-imidazole-5-methanol

Dihydroxyacetone dimer (28.9 g), followed by ethyl 2-(cyclopropyl) ethanimidate hydrochloride (30 g) were cautiously added portionwise to freshly condensed liquid ammonia (200 ml) at −78° under nitrogen. The resulting stirred slurry was poured into a cold dry ice autoclave (600 ml) and the mixture stirred and heated at 90° (600psi) for 16 h. The cooled (dry ice) mixture was poured into cold methanol (500 ml) and the mixture concentrated in vacuo to give a brown oil. The crude material was purified by flash column chromatogrpahy eluting with System C (100:8:1) to give the title compound as a colourless solid (14.71 g)

T.l.c. System C (100:8:1) Rf 0.2

INTERMEDIATE 66

4-chloro-2-(cyclopropylmethyl)-1H-imidazole-5-methanol

N-Chlorosuccinimide (12.1 g) was added to a solution of Intermediate 65 (12 g) in 2-methoxyethanol/dioxan 1:1 (200 ml) and the mixture stirred at room temperature, under nitrogen, in the dark for 6 h. The solvent was evaporated and the residue triturated under ethyl acetate and filtered to give the title compound as a colourless solid (7.25 g).

T.l.c. ether Rf 0.25

INTERMEDIATE 67

4-Chloro-2-(cyclopropylmethyl)-1H-imidazole-5-carboxaldehyde

Activated manganese dioxide (26.5 g) was added to a suspension of Intermediate 66 (26.5 g) in dichloromethane/1,4-dioxan 2:1 (300 ml) at room temperature under nitrogen, and the mixture heated at reflux for 16 h. The cooled mixture was filtered through hyflo and the filtrate evaporated to dryness. The residue was triturated under ether (30 ml) and filtered to give the title compound as a colourless solid (6.38 g).

T.l.c. ether:petroleum ether (1:1) Rf 0.4

INTERMEDIATE 68

1-[[3-Bromo-2-[2-[[(1,1-dimethylethoxy)carbonyl] amino]phenyl]-5-benzofuranyl] methyl-4-chloro-2-(cyclopropylmethyl)-1H-imidazole-5-carboxylic Acid Intermediate 36 (4 g) was treated with a mixture of sodium chlorite (5.58 g) and sodium dihydrogen phosphate (5.58 g) in water (60 ml) according to the method of Intermediate 24, to give the title compound as a colourless foam (4 g).

T.l.c. ether Rf 0.45 (streaking to 0.2).

INTERMEDIATE 69

Ethyl 1-[[3-bromo-2-[[(1,1-dimethylethoxy)carbonyl] amino]phenyl]-5-benzofuranyl] methyl]-4-chloro-2-(cyclopropylmethyl)-1H-imidazole-5-carboxylate DEAD (1.95 ml) was added dropwise to a mixture of Intermediate 68 (3.64 g), triphenylphosphine (3.25 g) and ethanol (1.14 g) in dry THF (100 ml) at room temperature under nitrogen. The mixture was stirred for 2 h, the solvent was then evaporated and the residue purified by flash column chromatography eluting with ether:petroleum ether (1:2) to give the title compound as a colourless foam (3.26 g).

T.l.c. ether:petroleum ether (2:1) Rf 0.25.

INTERMEDIATE 70

Methyl 2-[3-bromo-5-(bromomethyl)-2-benzofuranyl]benzoate

A solution of Intermediate 3 (0.26 g) in carbon tetrachloride (8 ml) was treated with 0NBS (0,134 g) and AIBN (10 mg) according to the method of Intermediate 6 to give the title compound as a pale yellow oil (0.19 g).

T.l.c. System A (1:9) Rf=0.4

INTERMEDIATE 71

5-Methyl-2-[(2-nitrophenyl)methoxy]benzaldehyde

Methanesulphonyl chloride (5.4 ml) was added dropwise to a stirred solution of 2-nitrobenzenemethanol (10.0 g) and triethylamine (10.1 ml) in 1,4-dioxane (10 ml) at 15°–25° C. After 30 min the mixture was filtered, washed with 1,4-dioxane (50 ml) and the filtrate added to a stirred mixture of 5-methylsalicylaldehyde (9.1 g) and potassium carbonate (9.9 g) in N,N-dimethylacetamide (50 ml). The mixture was stirred at 20° C. for 24 h, water (160 ml) was added and, after a further 1 h, the mixture was filtered. The filtrate was washed with water:1,4-dioxane (1:1; 50 ml) and water (150 ml) and dried at 40° C. in vacuo to give the title compound as a cream coloured solid (15.7 g) m.p. 124° C.

INTERMEDIATE 72

5-Methyl-2-(2-nitrophenyl)benzofuran

Sodium methoxide (0.45 g) was added to a suspension of Intermediate 71 (15.0 g) in N,N-dimethylacetamide (75 ml) at 25° C. and the mixture was stirred for 30 mins. Water (120 ml) and ethyl acetate (75 ml) was added and the aqueous layer was further extracted with ethyl acetate (75 ml and 25 ml). The combined ethyl acetate extracts were washed with water (75 ml) and aqueous sodium chloride (12%, 75 ml) and then concentrated to a volume of 25 ml. 98% Formic acid (75 ml) was added at 40° C. and the resulting solid collected by filtration to give the title compound as a yellow solid (13.7 g). m.p. 83° C.

INTERMEDIATE 73

3-Bromo-5-(bromomethyl)-2-(2-nitrophenyl)benzofuran

A mixture of Intermediate 72 (10.0 g), NBS (7.1 g) and 2,2'-azobis(2-methylpropionitrile) (0.26 g) in 1,1,1-trichloroethane (100 ml) was stirred and heated at reflux for 2.5 h. The mixture was cooled and dichloromethane (100 ml) was added. Bromine (2.84 ml) was added and the mixture stirred at room temperature for 18 h. Cyclohexene (10 ml) and dichloromethane (100 ml) was added, followed by water (100 ml), and the mixture stirred for 10 mins. The organic phase was evaporated, washed with 10% aqueous sodium thiosulphate (100 ml) and the combined aqueous washings further extracted with dichloromethane (50 ml). The combined organic extracts were washed with water (50 ml), the solvent evaporated, then ethyl acetate (25 ml) was added and the solvent re-evaporated. The resultant oil was dissolved in ethyl acetate (35 ml) and petroleum ether (200 ml) was added slowly. The suspension was cooled to 4° C. and the solid product collected by filtration. Recrystallisation from hot ethyl acetate (50 ml) and diisopropyl ether (150 ml) afforded the title compound as a yellow solid (6.1 g) m.p. 118° C.

INTERMEDIATE 74

Ethyl 1-[[3-bromo-2-(2-nitrophenyl)-5-benzofuranyl]methyl]-4-cyclopropyl-2-ethyl-1H-imidazole-5-carboxylate Intermediate 73 (75 g) and Intermediate 13 (38 g) were stirred in N,N'-dimethylacetamide (450 ml), potassium carbonate (50.4 g) was added and the mixture stirred at room temperature for 3 days. Ethyl acetate (750 ml) and water (750 ml) were added and the separated aqueous layer further extracted with ethyl acetate (750 ml). The combined organic extracts were washed with water (300 ml), 1M hydrochloric acid (300 ml), water (300 ml) and brine (300 ml). The ethyl acetate layer was evaporated in vacuo to a volume of 150 ml and the resulting suspension stirred overnight. Recrystallisation from diisopropyl ether (450 ml) afforded the title compound as a nearly white solid (74.3 g) m.p. 95° C.

INTERMEDIATE 75

Ethyl 5-cyclobutyl-4-oxazolecarboxylate

The title compound was prepared according to the method of Intermediate 12(a) from ethyl isocynoacetate and cyclobutylcarboxylic acid chloride.

T.l.c. System A (1:2) Rf=0.25

INTERMEDIATE 76

1-[[3-Bromo-2-(2-nitrophenyl)-5-benzofuranyl]methyl]-4-cyclopropyl-2-ethyl-5-iodo-1H-imidazole A stirred mixture of Intermediate 74 (2.18 g), 1N aqueous sodium hydroxide (40.5 ml), and methanol (122 ml) was heated at reflux for 2 h, the methanol was evaporated, brine (82 ml) and dichloromethane (112 ml) were added and the aqueous phase adjusted from pH 13.7 to pH 12.0 by addition of 5N hydrochloric acid. A solution of iodine (1.03 g) in dichloromethane (32 ml) was added dropwise to the stirred mixture over 3 min, keeping the aqueous phase between pH 11 and pH 12 by simultaneous dropwise addition of 1N aqueous sodium hydroxide. The mixture was stirred at ambient temperature for a further 5 min and the aqueous phase adjusted to pH 6.7 by addition of 5N hydrochloric acid. Aqueous sodium metabisulphite was added and the organic solution was dried and evaporated. The residue was purified by column chromatography eluting with System F (40:1). The resulting solid was crystallized from dichloromethane/diisopropyl ether to give the title compound as a yellow, crystalline solid (2.22 g) m.p. 180°–182°.

INTERMEDIATE 77

1-[[3-Bromo-2-(2-nitrophenyl)-5-benzofuranyl]methyl]-4-cyclopropyl-2-ethyl-1H-imidazole-5-carbonitrile-$^{13}$C A stirred mixture of Intermediate 76 (0.570 g), potassium [$^{13}$C] cyanide (0.051 g), and copper (I) iodide (0.030 g) in dry DMF (4 ml) was heated at 150° under nitrogen for 15 hours. Ethyl acetate (80 ml) was added and the resulting solution was washed with 1% w/v aqueous iron (III) chloride (160 ml). The aqueous phase was re-extracted with ethyl acetate (40 ml) and the combined organic phases was washed with water (160 ml), sodium metabisulphite (1 g) in water (160 ml), water (160 ml) and brine (160 ml) then dried and the residue purified by column chromatography eluting with ethyl acetate:cyclohexane (1:2). The residual oil was triturated with ether to give the title compound as a yellow crystalline solid (0.326 g) m.p. 116°–118°.

INTERMEDIATE 78

1-[[2-(2-Aminophenyl)-3-bromo-5-benzofuranyl]methyl]-4-cyclopropyl-2-ethyl-1H-imidazole-5-carbonitrile-$^{13}$C A mixture of Intermediate 77 (0.134 g), iron filings (3.0 g), acetic acid (0.85 ml), water (0.85 ml) and ethanol (25 ml) was stirred under reflux for 2.5 h. The mixture was filtered through celite which was then washed with dichloromethane (40 ml). The combined filtrates were evaporated and the residue was dissolved in dichloromethane (50 ml) washed with aqueous sodium bicarbonate (50 ml), dried and evaporated. The residue was purified by column chromatography eluting with System D (4:1). The resulting solid was recrystallised from acetonitrile (1 ml) to give the title compound as a white, crystalline solid (0.089 g) m.p. 168°–171°.

EXAMPLE 1

Ethyl 1-[[3-bromo-2-[2-(1H-tetrazol-5-yl)phenyl]-5-benzofuranyl]methyl]-4-cyclopropyl-2-ethyl-1H-imidazole-5-carboxylate Conc. Hydrochloric acid (0.5 ml) was added to a solution of Intermediate 19 (2.0 g) in ethanol/dichloromethane (1:1) (30 ml) and the mixture was stirred at room temperature for 11 h. Sodium bicarbonate (8%;10 ml) was added and the solvent evaporated. The residue was partitioned between water (10 ml) and ether (3×15 ml). The aqueous phase was acidified to pH1 with 2N HCl (ca 3 ml) and extracted with ethyl acetate (3×15 ml). The combined ethyl acetate extracts were washed with brine (20 ml) and dried. The solvent was evaporated to give the title compound as a colourless foam (1.17 g) m.p. 132°–137°.

T.l.c. System F (10:1) Rf 0.7.

Similarly prepared was:

EXAMPLE 2

1-[[3-Bromo-2-[2-(1H-tetrazol-5-yl)phenyl]-5-benzofuranyl]methyl]-2-cyclopropyl-4-methyl-1H-imidazole-5-carboxylic Acid n.m.r. (DMSOd$_6$) δ 1.0–1.1 (4H,m), 2.1–2.3 (1H,m), 2.4 (3H,s), 5.85 (2H,s), 7.18 (1H,dd), 7.33 (1H,brs), 7.54 (1H, d), 7.75–7.85 (2H,m), 7.9–8.0 (2H,m).

m.p. 190°–195° C. (dec).

From conc. hydrochloric acid (0.25 ml) and a solution of Intermediate 24 (700 mg) in (1:1) methanol/THF.

EXAMPLE 3

Ethyl 1-[[3-bromo-2-[2-[[(trifluoromethyl)sulphonyl]amino]phenyl]-5-benzofuranyl]methyl]-4-cyclopropyl-2-ethyl-1H-imidazole-5-carboxylate A 1M solution of trifluoromethanesulphonic anhydride in dichloromethane (4 ml) was added dropwise to a stirred solution of Intermediate 23 (2.01 g) in dichloromethane (45 ml) containing triethylamine (0.7 ml) at −73° under nitrogen. After stirring for 45 mins at −73°, further trifluoromethanesulphonic anhydride (1M in dichloromethane, 2 ml) was added dropwise. After 15 mins, water (15 ml) was added and the cooling bath removed. After warming to room temperature, further water (25 ml) was added and the separated organic phase was dried and concentrated in vacuo to afford a pink foam (2.4 g). Purification by chromatography (Neutral alumina, Grade 3) eluting with ether increasing to ether:acetic acid (49:1) afforded the title compound (1.75 g) as an off-white foam.

T.l.c. ether Rf 0.7 n.m.r. (DMSOd$_6$) δ 0.9–1.05 (m,4H), 1.12 (t,3H), 1.23 (t,3H), 2.6 (m, 1H), 2.73 (m, 2H), 4.25 (q,2H), 5.7 (s,2H), 7.1–7.7(m, 8H).

EXAMPLE 4

1-[[3-Bromo-2-[2-(1H-tetrazol-5-yl)phenyl]-5-benzofuranyl]methyl]-4-cyclopropyl-2-ethyl-1H-imidazole-5-carboxylic Acid Potassium hydroxide (1.2 g) in water (5 ml) was added to a suspension of the product of Example 1 (0.5 g) in ethanol (15 ml) and the mixture stirred at 55° for 18 h. The solvent was evaporated and the residue partitioned between water (25 ml) and ether (3×25 ml). The aqueous phase was acidified to pH1 with hydrochloric acid (2N, 15 ml) and extracted with ethyl acetate (3×30 ml). The combined ethyl acetate extracts were washed with brine (50 ml) and dried. The solvent was concentrated in vacuo resulting in the precipitation of a colourless solid which was filtered off and washed with ether (2×5 ml) to give the title compound as a colourless solid (290 mg) m.p. 198°.

n.m.r. (DMSOd$_6$) δ 0.93 (d,2H), 1.12 (t,3H), 2.68 (q+m; 4H), 5.71 (s,2H), 7.06 (dd,1H), 7.12 (S,1H), 7.53 (d, 1H), 7.81 (m,2H), 7.95 (m, 2H).

EXAMPLE 5

1-[[3-Bromo-2-[2-[[(trifluoromethyl)sulphonyl]amino]phenyl]-5-benzofuranyl]methyl]-4-cyclopropyl-2-ethyl-1H-imidazole-5-carboxylic Acid A mixture of the product of Example 3 (1.72 g) and 2N aqueous sodium hydroxide (15 ml) in methanol (30 ml) was stirred at room temperature for 6 h. After standing overnight, the solution was diluted with further 2N aqueous sodium hydroxide (10 ml), stirred for a further 2 h at room temperature and then heated at 40° for 90 mins. After cooling, the solution was diluted with brine (80 ml) and water (50 ml) before being washed with ether (100 ml). The aqueous phase was then acidified with 2N hydrochloric acid to pH1 and the cloudy solution was extracted with ethyl acetate (3×90 ml). The combined ethyl acetate extracts were dried and concentrated in vacuo to afford the title compound (1.72 g) as an off-white foam.

T.l.c. System F(10:1) Rf=0.45 (streaking to 0.25)

n.m.r. (DMSOd$_6$) δ 1.1–1.2 (m,7H), 2.7 (m, 1H), 3.0 (q,2H), 5.88 (s,2H), 7.2 (dd, 1H), 7.4–7.8 (m, 6H).

EXAMPLE 6

1-[[3-Bromo-2-[2-[[(trifluoromethyl)sulphonyl]amino ]phenyl]-5-benzofuranyl]methyl]-4-cyclopropyl-2-ethyl-1H-imidazole-5-carboxamide Concentrated aqueous ammonia (10 ml) was added to a solution of Intermediate 26 (0.4 g) in ethanol (10 ml) and the mixture stirred for 16 h at room temperature. The ethanol was evaporated in vacuo and the residue partitioned between hydrochloric acid (0.5M; 25 ml) and ethyl acetate/ethanol (10:1) (3×25 ml). The combined organic extracts were washed with water (2×25 ml) and dried. The solvent was evaporated in vacuo to give a colourless foam which was triturated under ether (3×10 ml) to give the title compound as a colourless solid (251 mg).

T.l.c. System F (10:1) Rf 0.5.

n.m.r. (DMSOd$_6$) δ0.95–1.15 (m+t;7H), 2.21 (m, 1H), 3.05 (q,2H), 5.77 (s,2H), 7.27 (dd, 1H), 7.48–7.75 (m, 6H), 8.13 (brs,2H).

Example 6 was also prepared by the following alternative method:

EXAMPLE 6 (ALTERNATIVE METHOD)

1-[[3-Bromo-2-[2-[[(trifluoromethyl)sulphonyl]amino]phenyl]-5-benzofuranyl]methyl]-4-cyclopropyl-2-ethyl-1H-imidazole-5-carboxamide 1,1'-Carbonyldiimidazole (14.3 g) was added in one portion to a solution of the product of Example 5 (18 g) in dry THF (600 ml) at room temperature under nitrogen. The mixture was stirred for 16 h, then ammonia was bubbled through the solution for 30 mins, and the mixture then stirred for 5 h. Ammonia was again bubbled through the reaction mixture for 30 mins, and the solution stirred for a further 16 h. The reaction mixture was diluted with ethyl acetate (1 liter) and cooled in an ice-bath. Cold dilute hydrochloric acid (0.25M ca. 1 liter) was added dropwise to the vigorously stirred reaction mixture until pH6 was achieved. The aqueous phase was separated and extracted further with ethyl acetate (3×500 ml). The combined organic extracts were washed with brine (2×800 ml) and dried. The solvent was evaporated to give a colourless foam (18 g) which was triturated under ether (250 ml) and filtered to give a colourless amorphous solid (13.8 g), m.p. 155.6°–159.2°.

T.l.c. System F (10:1) Rf 0.5

EXAMPLE 7

1-[[3-Bromo-2-[2-[[(trifluoromethyl)sulphonyl]amino]phenyl]-5-benzofuranyl]methyl]-4-cyclopropyl-2-ethyl-N-methyl-1H-imidazole-5-carboxamide A mixture of Intermediate 26 (0.48 g) in ethanol (5 ml) and 40% aqueous methylamine (20 ml) was heated at reflux for 6 h. After cooling, the mixture was partitioned between ethyl acetate (60 ml), brine (30 ml) and water (20 ml). The separated aqueous phase was further extracted with ethyl acetate (50 ml) and the combined organic extracts were washed with 1N hydrochloric acid (2×50 ml), water (2×50 ml) dried and concentrated in vacuo to afford the title compound (0.31 g) as a white solid.

T.l.c. System F (9:1), Rf 0.75.

n.m.r (DMSOd$_6$) δ0.8–1.05 (m,4H), 1.2 (t,3H), 2.07 (m, 1H), 2.79 (d,3H), 3.0 (q,2H), 5.63 (s,2H), 7.0–7.6 (m, 8H), 8.6 (m, 1H).

EXAMPLE 8

1-[[3-Bromo-2-[2-[[(trifluoromethyl)sulphonyl]amino]phenyl]-5-benzofuranyl]methyl]-4-cyclopropyl-2,N,diethyl-1H-imidazole-5-carboxamide A solution of Intermediate 26 (300 mg), THF (10 ml) and ethylamine 70% solution in water (2 ml) was stirred at room temperature for 18 hours. The solvent was removed in vacuo and the residue dissolved in ethyl acetate (15 ml). The ethyl acetate layer was washed with brine (3×15 ml), dried and concentrated in vacuo to give an oil. This was purified by flash column chromatography, eluting with System F (20:1) to afford the title compound as an off-white solid (110 mg).

T.l.c. System F (10:1) Rf 0.48 m.p. 124°–130° C.

EXAMPLE 9

1-[[3-Bromo-2-[2-(1H-tetrazol-5-yl)phenyl]-5-benzofuranyl]methyl]-2-ethoxy-4-methyl-1H-imidazole-5-carboxaldehyde From Intermediate 25 (180 mg) and conc. HCl (0.5 ml) in methanol/THF (1:1) (20 ml) according to the method of Example 1. Purification by column chromatography eluting with dichloromethane:ether:hexane: acetic acid (100:100:100:15) gave the title compound as a white solid (20 mg).

T.l.c. System E (10:10:1) Rf 0.46 n.m.r. (CDCl$_3$) δ 1.29 (3H,t), 2.12 (3H,s), 4.25 (2H,q), 5.27 (2H,s), 7.1–7.4 (3H,m), 7.5–7.7 (2H,m), 7.84 (1H,m), 7.96 (1H,m).

Examples 10 to 12 in Table 3 were prepared according to the method of Example 3 (Equation 3):

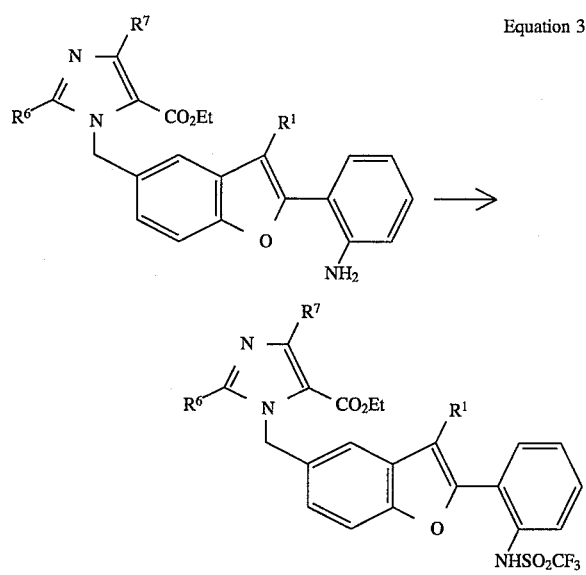

Equation 3

Examples 13 to 20 in Table 4 were prepared according to the method of Example 5 (Equation 4):

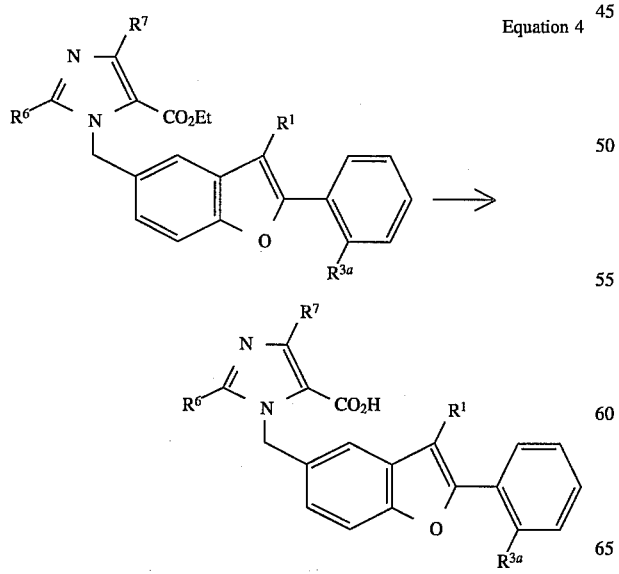

Equation 4

Examples 21 and 22 in Table 5 were prepared according to the alternative method of Example 6, utilising ammonia or the appropriate alkylamine (Equation 5):

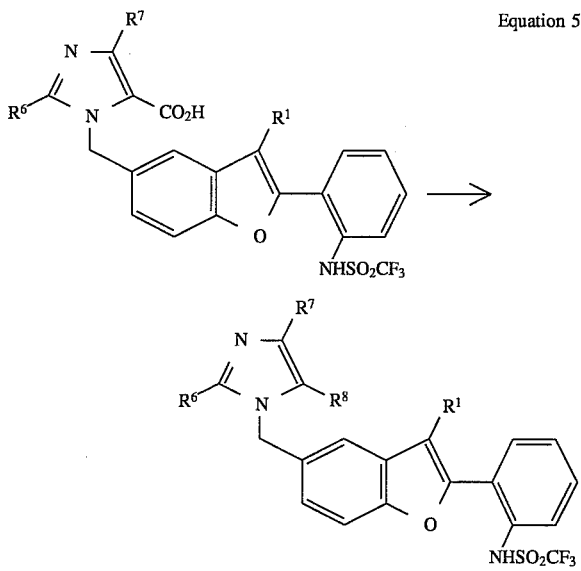

Equation 5

Examples 23 to 34 in Table 6 were prepared according to the alternative method of Example 6, utilising ammonia or the appropriate alkylamine (Equation 6):

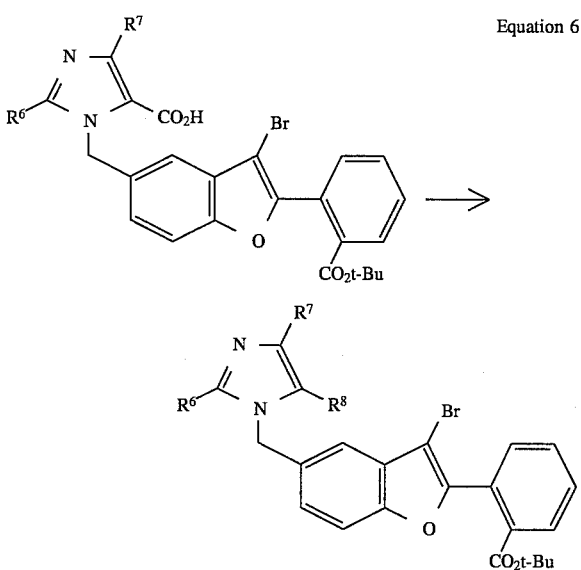

Equation 6

EXAMPLE 35

2-[3-Bromo-5-[[4-cyclopropyl-2-ethyl-5-[(ethylamino)carbonyl]-1H-imidazol-1-yl]methyl]-2-benzofuranyl]benzoic Acid A solution of the product of Example 24 (0.175 g) in dry trifluoroacetic acid (4 ml) was stirred at ambient temperature for 1.5 h. The solvent was evaporated in vacuo. The residue was dissolved in dichloromethane (50 ml) and washed with water (50 ml) (pH adjusted to 5 with aqueous sodium carbonate). The organic extract was dried and evaporated to give a solid residue which was crystallized from ethyl acetate/hexane to give the title compound as a white solid (0.12 g) m.p. 182°–4°.

T.l.c. System F (10:1) Rf=0.4.

Examples 36 to 49 and 66 in Table 7 were prepared according to the method of Example 35 (Equation 7):

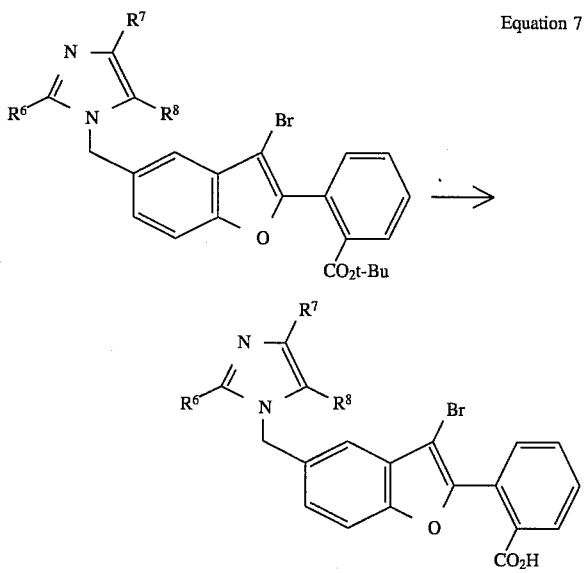

Equation 7

Examples 50 to 57 in Table 8 were prepared according to the alternative method of Example 6, utilizing the appropriate alkylamine (Equation 8):

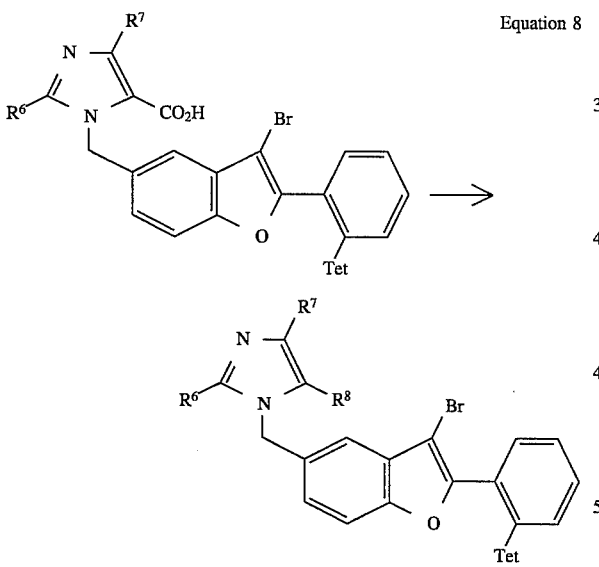

Equation 8

Example 58

4-Cyclopropyl-N,2-diethyl-1-[[2-[2-[[(trifluoromethyl)sulphonyl]amino]phenyl]-5-benzofuranyl]methyl]-1H-imidazole-5-carboxamide A solution of the product of Example 8 (0.25 g) in ethyl acetate (15 ml) was stirred under a hydrogen atmosphere over 10% palladium on carbon (0.3 g; 50% aqueous paste) at room temperature for 3 h. Solid sodium carbonate (70 mg) was added and the reaction continued for a further 4 h. The mixture was filtered and the filtrate evaporated. The residue was purified by column chromatography eluting with System F (20:1) increasing to (5:1) to give the title compound as a white powder (0.11 g), m.p. 165°–172°.

T.l.c. System F (9:1) Rf 0.65

EXAMPLE 59a

1-[[3-Bromo-2-[2-[[(trifluoromethyl)sulphonyl]amino]phenyl]-5benzofuranyl]methyl]-4-cyclopropyl-2-ethyl-1H-imidazole-5-carboxamide, Sodium Salt Sodium hydroxide (0.25M in ethanol; 3.27 ml) was added dropwise to a solution of the product of Example 6 (0.5 g) at 60° under nitrogen. The solution was cooled to room temperature, then concentrated in vacuo (to 3 ml). Ether (20 ml) was added, resulting in the precipitation of a colourless powder. The ether was decanted and fresh ether (20 ml) added. The solid was filtered and dried to give the title compound as a colourless solid (397 mg).

n.m.r. (DMSOd$_6$) δ 0.88 (4H,m), 1.15(3H,t), 2.17 (1H,m), 2.77(2H,q), 5.61 (1H,s), 6.91 (1H,m), 7.11(1H,dd), 7.29 (3H,m), 7.50 (2H,m), 7.62 (2H,br.s).

Assay Found: C,44.4; H,3.3; N,8.0;

$C_{25}H_{21}BrF_3NaN_4O_4S.2H_2O$ requires: C,44.85; H,3.7; N,8.4%

EXAMPLE 59b

1-[[3-Bromo-2-[2-[[(trifluoromethyl)sulphonyl]amino]phenyl]-5-benzofuranyl]methyl]-4-cyclopropyl-2-ethyl-1H-imidazole- 5-5-carboxamide, Potassium Salt Potassium hydroxide (1M in ethanol; 0.16 ml) was added to a solution of the product of Example 6 (0.1 g) in ethanol (5 ml) at room temperature. The mixture was stirred for 1 h, and the solvent concentrated in vacuo (to 0.5 ml). Ether (5 ml) was added, resulting in the precipitation of a colourless solid which was filtered off, washed with ether (2×5 ml) and dried to give the title compound as a colourless solid (70 mg).

n.m.r. (DMSOd$_6$) δ 0.90 (4H,m), 1.15(3H,t), 2.16 (1H,m), 2.81 (2H,q), 5.62 (1H,s), 6.92 (1H,m), 7.13 (1H,dd), 7.30(3H,m), 7.45 (1H,d), 7.55 (1H,d), 7.71 (2H,br.s).

Assay Found: C,43.55; H,3.7; N,7.7;

$C_{25}H_{21}BrF_3KN_4O_4S.2.5H_2O$ requires: C,43.2; H,3.8; N,8.1%

EXAMPLE 59c

1-[[3-Bromo-2-[2-[[(trifluoromethyl)sulphonyl]amino]phenyl]-5-benzofuranyl]methyl]-4-cyclopropyl-2-ethyl-1H-imidazole-5-carboxamide, Ammonium Salt Concentrated aqueous ammonia (0.2 ml) was added to a solution of the product of Example 6 (50 mg) in ethanol (1 ml) at room temperature. The mixture was stirred for 30 min, then the solvent was evaporated. The residue was triturated under ether (2 ml) and filtered to give the title compound as a colourless solid (50 mg), m.p. 135°–142°.

Assay Found: C,45.4; H,4.4; N,10.4;

$C_{25}H_{25}BrF_3N_5O_4S.2H_2O$ requires: C, 45.2; H, 4.4; N, 10.5%

Examples 60 and 61 in Table 9 were prepared according to the method of Example 35. Examples 62 and 63 in Table 9 were prepared according to the alternative method of Example 6 using ammonia. Examples 64 and 65 in Table 9 were prepared according to the method of Example 5 (see Table 9 with reference to the formula shown below):

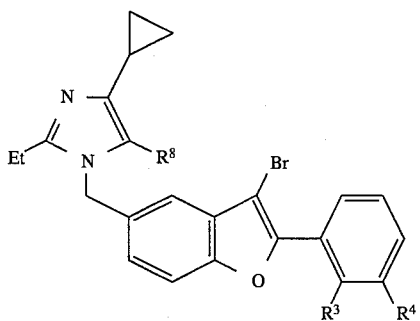

[Examples 60 and 61: $R^8=CO_2t$—Bu→$CO_2H$;
Examples 62 and 63: $R^8=CO_2H$→$CONH_2$; and
Examples 64 and 65: $R^3=CO_2Me$→$CO_2H$].

Example 68

Ethyl 4-cyclopropyl-2-ethyl-1-[[3-methoxycarbonyl-2-[2-(methoxycarbonyl)phenyl]-5-benzofuranyl]methyl]-1H-imidazole-5-carboxylate Triethylamine (0.56 ml) was added to a solution of the product of Example 67 (see Table 2c) (1 g) in DMF (10 ml), methanol (10 ml) and THF (3 ml). Palladium acetate (163 mg) and 1,3 bis(diphenylphosphino)propane (299 mg) were added and the system sealed under carbon monoxide. After heating at 75° C. for 25 h the solution was concentrated in vacuo and partitioned between ethyl acetate (50 ml) and 10% lithium chloride solution (2×50 ml). The dried organic layer was concentrated in vacuo and the residue purified by flash chromatography eluting with System A (3:2) to give the title compound as a white foam (551 mg). m.p. 105°–110° C. (decomp)

T.l.c. System A (2:1) Rf 0.38

EXAMPLE 69

1,1-Dimethylethyl 2-[3-bromo-5-[(2-ethyl-4-cyclopropyl-1H-imidazol-1-yl)methyl-2-benzofuranylbenzoate The product of Example 17 (100 mg) was placed in a flask and stirred at 160° C. for 1.5 h (40° C. above melting point). The resulting gum was dissolved in ethyl acetate (25 ml), washed with water (2×25 ml), dried and evaporated to give the title compound as an orange gum (58 mg).

T.l.c. System G(90:10:1) Rf=0.46 n.m.r. ($CDCl_3$) δ 0.69 (m,2H), 0.82 (m,2H), 1.24–1.28 (m, 12H), 1.85 (m, 1H), 2.68 (q,2H), 5.1 (s,1H), 6.5 (s,1H), 7.07 (m, 1H), 7.32 (d, 1H), 7.42 (d, 1H), 7.59 (m,2H), 7.7 (m, 1H), 7.95 (m, 1H).

Similarly prepared was:

EXAMPLE 70

N-[2-[3-Bromo-5-[(2-ethyl-4-cyclopropyl-1H-imidazol-1-yl)methyl]- 2-benzofuranyl]phenyl]-2,2,2-trifluoromethanesulphonamide From the product of Example 5. m.p. 284°–285° C.

T.l.c. System F (9:1) Rf=0.38

EXAMPLE 71

N-[2-[3-Bromo-5-[[5-(cyano-$^{13}$C)-4-cyclopropyl-2-ethyl-1H-imidazol-1-yl] methyl]-2-benzofuranyl]phenyl]-2,2,2-trifluoromethanesulphonamide A solution of Intermediate 78 (0.066 g) and triethylamine (0.029 g) in dichloromethane (27 ml) was cooled to −70° with stirring under nitrogen. A solution of trifluoromethanesulphonic anhydride (0.045 g) in dichloromethane (1.8 ml) was added and the mixture allowed to warm to ambient temperature. Triethylamine (0.015 g) in dichloromethane (1 ml) then trifluoromethanesulphonic anhydride (0.0235 g) in dichloromethane (0.9 ml) were added. The mixture was cooled to −70° and trifluoromethanesulphonic anhydride (0.0235 mg) in dichloromethane (0.9 ml) added. The mixture was again allowed to warm to ambient temperature. Water (50 ml) was added and 1N aqueous sodium hydroxide added to adjust the aqueous phase from pH 1 to pH 5. The dichloromethane phase was dried. The solvent was evaporated and the residue was purified by column chromatography eluting with System F (20:1). The residue was triturated with ether to give the title compound as a beige foam (0.066 g).

T.l.c. System F (10:1) Rf 0.64 vmax (nujol) 2161, 1203, 1143, 603 $cm^{-1}$.

EXAMPLE 72

1-[[3-Bromo-2-[2-[[(trifluoromethyl)sulphonyl]amino]phenyl]-5-benzofuranyl] methyl]-4-cyclopropyl-2-ethyl-1H-imidazole-5carboxamide-$^{13}$C To the product of Example 71 (0.253 g) was added concentrated aqueous ammonia:water 1:1 (26 ml), methanol (5 ml) and 27.5% w/v hydrogen peroxide (11 ml) and the mixture was stirred at ambient temperature for 80 minutes. Ethyl acetate (150 ml) and water (100 ml) were added and the aqueous phase acidified from pH 10.8 to pH 2.0 by cautious addition of 11N hydrochloric acid (20 ml). The organic extract was washed sequentially with sodium metabisulphite (9 g) in water (100 ml), water (100 ml) and brine (100 ml) and then dried. Solvent was evaporated and the residue purified by column chromatography eluting with System F (10:1). The residue was crystallized from a mixture of ethanol and water to give the title compound as a white, crystalline solid (0.167 g) m.p. 208°–210°.

T.l.c. System F (5:1) Rf 0.62.

EXAMPLE 73

Ethyl 1-[[2-[2-[[(trifluoromethyl)sulphonyl]amino]phenyl]-5-benzofuranyl] methyl]-4-cyclopropyl-2-ethyl-1H-imidazole-5-carboxylate The title compound was isolated from the product of Intermediate 40 and was purified by column chromatogrpahy eluting with System A (1:1). m.p. 98°–102° C.

T.l.c. ether Rf=0.6

The compounds of the invention are tested in vitro for angiotensin II receptor antagonism. Aortic strips are obtained from male New Zealand white rabbits and prepared for recording isometric contractions in response to cumulative addition of angiotensin II. The potencies of test antagonists are assessed by measuring their abilities to displace the angiotensin II cumulative concentration response curve. The method used is that of Ackerly et al., *Proc. Natl. Acad. Sci.*, 74(12), pp 5725–28 (1977) with the exception that the final composition of the physiological salt solution is as given below in Table 1:

TABLE 1

| Ingredient | Amount (mM) |
|---|---|
| $Na^+$ | 143.4 |
| $K^+$ | 5.9 |
| $Mg^{2+}$ | 0.6 |
| $Ca^{2+}$ | 1.3 |
| $Cl^-$ | 124.5 |
| $HPO_4^-$ | 1.2 |
| $SO_4^{2-}$ | 0.6 |
| $HCO_3^-$ | 25.0 |
| glucose | 11.1 |
| indomethacin | 0.005 |
| ascorbic acid | 0.1 |

The tissues are initially challenged with $K^+$ (80 mM) and then washed at 0, 5, 10 and 15 minutes after the response to $K^+$ has plateaued. After a further 45 minutes an angiotensin II cumulative response curve is constructed (0.1 nM to 0.1 μM in 10-fold increments) and the tissues are washed as before. A second, third and fourth angiotensin II cumulative response curve (0.1 nM to 0.1 μM in 3-fold increments) is then constructed at hourly intervals (15 minutes washing after each curve followed by 45 minutes equilibration). The compounds of the invention (30 μM) are tested for angiotensin II receptor antagonism by application 45 minutes before construction of the fourth angiotensin II curve. The third and fourth angiotensin II curves are expressed graphically and a concentration ratio (CR) is calculated by dividing the angiotensin II $EC_{50}$ value obtained in the presence of the test antagonist (i.e. fourth curve) by the angiotensin II $EC_{50}$ value obtained in the absence of the test antagonist (i.e. third curve).

The potency of the test antagonist is expressed as a pKb which is calculated from the equation:

$$pKb = -\log \left[ \frac{CR - 1}{[\text{antagonist}]} \right]$$

which is a rearrangement of equation 4 described by Furchgott, in *Handbook of Exp. Pharmacol.*, 33, p 290 (1972) (eds. Blaschko and Muscholl).

If a compound supresses the maximum response to angiotensin II, a pKb is estimated using the double reciprocal plot technique for insurmountable antagonists, described by T. P. Kenakin, *Pharmacol. Rev.*, 36(3), pp 165–222 (esp. 203–204) (1984).

Compounds of the invention will desirably exhibit a pKb in the range between 5 and 12. Thus we have found that the compounds of the invention inhibit the action of the hormone angiotensin II and are therefore useful in the treatment of conditions in which it is desirable to inhibit angiotensin II activity. In particular, the compounds of the Examples are active in the above test.

There is thus provided as a further aspect of the invention a compound of general formula (I) or a physiologically acceptable salt, solvate or metabolically labile ester thereof for use in the treatment of conditions associated with excessive or unregulated angiotensin II activity.

In a further or alternative aspect of the invention there is provided a compound of general formula (I) or a physiologically acceptable salt, solvate or metabolically labile ester thereof for the manufacture of a therapeutic agent for the treatment of conditions associated with excessive or unregulated angiotensin II activity.

There is also provided in a further or alternative aspect of the invention a method for the treatment of conditions associated with excessive or unregulated angiotensin II activity in a mammal including man comprising administration of an effective amount to a mammal in need of such treatment a compound of general formula (I) or a physiologically acceptable salt, solvate or metabolically labile ester thereof.

In addition, by virtue of their antagonistic activity at angiotensin II receptors, compounds of the present invention will be of value in the treatment of conditions associated with activation of the Renin-Angiotensin System.

There is thus provided a further aspect of the present invention a compound of general formula (I) or a physiologically acceptable salt, solvate or metabolically labile ester thereof for use in the treatment of a condition associated with activation of the Renin-Angiotensin system.

In a further or alternative aspect of the present invention there is provided a compound of general formula (I) or a physiologically acceptable salt, solvate or metabolically labile ester thereof for the manufacture of a therapeutic agent for the treatment of a condition associated with activation of the Renin-Angiotensin System.

There is also provided in a further or alternative aspect of the present inventions a method for the treatment of a condition associated with the activation of the Renin-Angiotensin System in a mammal including man comprising administration of an effective amount to a mammal in need of such treatment of a compound of general formula (I) or a physiologically acceptable salt, solvate or metabolically labile ester thereof.

The following examples illustrate pharmaceutical formulations according to the invention. The term "active ingredient" is used herein to represent a compound of formula (I).

PHARMACEUTICAL EXAMPLE 1

| Oral Tablet A | |
|---|---|
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

PHARMACEUTICAL EXAMPLE 2

| Oral Tablet B | |
|---|---|
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

PHARMACEUTICAL EXAMPLE 3

| Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

PHARMACEUTICAL EXAMPLE 4

| Injection Formulation | |
|---|---|
|  | % w/v |
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

TABLE 1a (see Equation 1a)

| Int. No. | From: | $R^3$ | $R^6$ | $R^7$ | Data |
|---|---|---|---|---|---|
| 29 | Ints. 28 + 57 | $CO_2$t-Bu | n-Pr | c-Pr | T.l.c. System A (1:3) Rf = 0.19 |
| 30 | Ints. 28 + 60 | $CO_2$t-Bu | n-Bu | c-Pr | Assay*[1],*[2] |
| 31 | Ints. 28 + 59 | $CO_2$t-Bu | n-Pr | c-Bu | m.p. 118–120° C. |
| 32 | Ints. 11 + 57 | Tet-P | n-Pr | c-Pr | T.l.c. System A (2:1) Rf = 0.53 |
| 33 | Ints. 28 + 13 | $CO_2$t-Bu | Et | c-Pr | T.l.c. System A (1:1) Rf = 0.3 |
| 34 | Ints. 28 + 61 | $CO_2$t-Bu | —$CH_2$-c-Bu | $CF_3$ | T.l.c. System A (1:3) Rf = 0.4 |
| 35 | Ints. 6 + 58 | NHt-BOC | —$CH_2$-c-Bu | i-Pr | T.l.c. System A (1:3) Rf = 0.28 |
| 36*[18] | Ints. 6 + 67 | NHt-BOC | —$CH_2$-c-Pr | Cl | T.l.c. pet.ether:ether (1:1) Rf = 0.4 |

TABLE 1b (see Equation 1b)

| Int. No. | From: | $R^1$ | $R^6$ | $R^7$ | Data |
|---|---|---|---|---|---|
| 37 | Int. 42 | Et | Et | c-Pr | T.l.c. System C (150:8:1) Rf = 0.5 |
| 38 | Int. 35 | Br | —$CH_2$-c-Bu | i-Pr | T.l.c. System A (1:1) Rf = 0.36 |
| 39 | Int. 69 | Br | —$CH_2$-c-Pr | Cl | T.l.c ether Rf = 0.25 |

TABLE 2a (see Equation 2a)

| Int. No. | From | $R^3$ | $R^4$ | Data |
|---|---|---|---|---|
| 46 | Int. 43 | $CO_2$t-Bu | F | Assay found: C, 73.1; H, 5.8; $C_{20}H_{19}FO_3$ req: C, 73.6; H, 5.9% |
| 47 | Int. 43 | $CO_2$t-Bu | Cl | Assay found: C, 70.1; H, 5.6; $C_{20}H_{19}ClO_3$ req: C, 70.1; H, 5.6% |
| 48 | Int. 43 | $CO_2$Me | Cl | T.l.c. System I (1:3) Rf = 0.75 |

TABLE 2b (see Equation 2b)

| Int. No. | From | $R^1$ | $R^3$ | $R^4$ | Data |
|---|---|---|---|---|---|
| 49 | Int. 45 | Br | $CO_2$Me | F | T.l.c. System A (1:3) Rf = 0.4 |

TABLE 2b-continued (see Equation 2b)

| Int. No. | From | $R^1$ | $R^3$ | $R^4$ | Data |
|---|---|---|---|---|---|
| 50 | Int. 46 | H | $CO_2$t-Bu | F | T.l.c. System A (1:4) Rf = 0.45 |
| 51 | Int. 47 | H | $CO_2$t-Bu | Cl | T.l.c System A (1:6) Rf = 0.5 |
| 52 | Int. 48 | Br | $CO_2$Me | Cl | T.l.c. System A (1:1) Rf = 0.85 |

TABLE 2c (see Equation 2c)

| Int. No. | From: | $R^1$ | $R^3$ | $R^4$ | $R^8$ | Data |
|---|---|---|---|---|---|---|
| 53 | Ints. 49 + 64 | Br | $CO_2$Me | F | $CO_2$t-Bu | T.l.c. System A (2:1) Rf = 0.6 |
| 54 | Ints. 50 + 13 | H | $CO_2$t-Bu | F | $CO_2$Et | T.l.c. System A (1:1) Rf = 0.4 |
| 55 | Ints. 51 + 13 | H | $CO_2$t-Bu | Cl | $CO_2$Et | n.m.r.*[15] |
| 56 | Ints. 52 + 64 | Br | $CO_2$Me | Cl | $CO_2$t-Bu | n.m.r.*[20] |
| Ex. No. 67 | Ints. 70 + 13 | Br | $CO_2$Me | H | $CO_2$Et | T.l.c. System A (1:1) Rf = 0.15 m.p. 145–146° C. |

TABLE 3

(see Equation 3)

| Ex. No. | From: | $R^1$ | $R^6$ | $R^7$ | Data |
|---|---|---|---|---|---|
| 10 | Int. 37 | Et | Et | c-Pr | T.l.c. System A (2:1) Rf = 0.44 |
| 11 | Int. 38 | Br | —$CH_2$-c-Bu | i-Pr | m.p. 92–94° C. T.l.c. System A (1:1) Rf = 0.43 n.m.r.*[19] |
| 12 | Int. 39 | Br | —$CH_2$-c-Pr | Cl | T.l.c. ether:acetic acid (50:1) Rf = 0.5 m.p. 76–81° C. |

TABLE 4

(see Equation 4)

| Ex. No. | From: | $R^1$ | $R^{3a}$ | $R^6$ | $R^7$ | T.l.c System | Rf = | m.p. | Other |
|---|---|---|---|---|---|---|---|---|---|
| 13 | Int. 29 | Br | $CO_2$t-Bu | n-Pr | c-Pr | G(200:5:2) | 0.13 | | Assay*[3] |
| 14 | Int. 30 | Br | $CO_2$t-Bu | n-Bu | c-Pr | | | 109–115° C. | Assay*[4] |
| 15 | Int. 31 | Br | $CO_2$t-Bu | n-Pr | c-Bu | F(9:1) | 0.44 | 134–136° C. | |
| 16 | Int. 32 | Br | Tet | n-Pr | c-Pr | G(100:10:5) | 0.32 | | n.m.r.*[5],*[6] |
| 17 | Int. 33 | Br | $CO_2$t-Bu | Et | c-Pr | F(10:1) | 0.5 | 118–121° C. | |
| 18 | Ex. 15 | Br | $CO_2$H | n-Pr | c-Bu | F(9:1) | 0.26 | 172–174° C. | |
| 19 | Ex. 10 | Et | $NHSO_2CF_3$ | Et | c-Pr | G(100:10:2) | 0.54 | 159–164° C. (decomp) | |
| 20 | Ex. 68 | $CO_2$H | $CO_2$H | Et | c-Pr | | | 235–238° C. | Mass Spec. MH$^+$(calc(475 MH$^+$(obs)475 |
| 74 | Ex. 11 | Br | $NHSO_2CF_3$ | —$CH_2$-c-Bu | i-Pr | F(9:1) | 0.55 | 180–182° C. (decomp) | |
| 75 | Ex. 12 | Br | $NHSO_2CF_3$ | —$CH_2$-c-Pr | Cl | F(100:6) | 0.45 | | n.m.r.*[22] |

TABLE 5

(see Equation 5)

| Ex. No | From: | $R^1$ | $R^6$ | $R^7$ | $R^8$ | T.l.c. System | Rf = | m.p. | Other |
|---|---|---|---|---|---|---|---|---|---|
| 21 | Ex. 10 | Et | Et | c-Pr | $CONH_2$ | F(10:1) | 0.7 | 130–135° C. | |
| 22 | Ex. 5 | Br | Et | c-Pr | $CON(CH_3)_2$ | F(9:1) | 0.53 | | Assay[7] |
| 76 | Ex. 74 | Br | —$CH_2$-c-Bu | i-Pr | $CONH_2$ | F(9:1) | 0.53 | | Assay[26] |
| 77 | Ex. 75 | Br | —$CH_2$-c-Pr | Cl | $CONH_2$ | F(100:6) | 0.45 | | n.m.r.[23] |

TABLE 6

(see Equation 6)

| Ex. No. | From: | $R^6$ | $R^7$ | $R^8$ | T.l.c. System | Rf = | m.p. | Other |
|---|---|---|---|---|---|---|---|---|
| 23 | Ex. 17 | Et | c-Pr | CONHi—Pr | A (3:1) | 0.19 | 125–127° C. | |
| 24 | Ex. 17 | Et | c-Pr | CONHEt | ether | 0.5 | 132–133° C. | |
| 25 | Ex. 13 | n-Pr | c-Pr | CONHEt | G (90:10:1) | 0.48 | | [8] |
| 26 | Ex. 14 | n-Bu | c-Pr | CON⟨─O⟩ | F (10:1) | 0.7 | | [9] |
| 27 | Ex. 14 | n-Bu | c-Pr | $CONH_2$ | F (10:1) | 0.7 | 106–108° C. | |
| 28 | Ex. 15 | n-Pr | c-Bu | $CONH_2$ | J (1:1) | 0.22 | | [10] |
| 29 | Ex. 15 | n-Pr | c-Bu | CONHEt | J (1:1) | 0.4 | | [11] |
| 30 | Ex. 17 | Et | c-Pr | $CONHCH_2CF_3$ | ether | 0.49 | 129–132° C. | |
| 31 | Ex. 17 | Et | c-Pr | $CONHCH_2Ph$ | ether | 0.5 | 146–148° C. | |
| 32 | Ex. 17 | Et | c-Pr | $CONHCH_2$-c-Pr | G (45:5:1) | 0.66 | | [12] |
| 33 | Ex. 13 | n-Pr | c-Pr | $CONHCH_2Py$ | I (4:1) | 0.27 | | [13] |
| 34 | Ex. 17 | Et | c-Pr | $CONHSO_2Ph$ | F (10:1) | 0.4 | | [14] |

TABLE 7

(see Equation 7)

| Ex. No. | From: | $R^6$ | $R^7$ | $R^8$ | T.l.c. System | Rf = | m.p. | Other |
|---|---|---|---|---|---|---|---|---|
| 36 | Ex. 23 | Et | c-Pr | CONHi—Pr | G (90:10:1) | 0.48 | 232–234° C. | |
| 37 | Ex. 13 | n-Pr | c-Pr | $CO_2H$ | G (90:10:1) | 0.3 | 159–161° C. | |
| 38 | Ex. 25 | n-Pr | c-Pr | CONHEt | G (90:10:1) | 0.32 | 179–181° C. | |
| 39 | Int. 33 | Et | c-Pr | $CO_2Et$ | F (10:1) | 0.45 | 210–212° C. | |
| 40 | Ex. 26 | n-Bu | c-Pr | CON⟨─O⟩ | F (10:1) | 0.55 | 125–129° C. | |
| 41 | Ex. 27 | n-Bu | c-Pr | $CONH_2$ | F (10:1) | 0.4 | 234–236° C. | |
| 42 | Ex. 30 | Et | c-Pr | $CONHCH_2CF_3$ | H (100:1) | 0.33 | 234–235° C. | |
| 43 | Ex. 28 | n-Pr | c-Bu | $CONH_2$ | F (9:1) | 0.63 | 222–223° C. | |
| 44 | Ex. 29 | n-Pr | c-Bu | CONHEt | F (9:1) | 0.53 | 195–196° C. | |
| 45 | Int. 34 | —$CH_2$-c-Bu | $CF_3$ | $CO_2Et$ | A (1:1) | 0.6 | 92–94° C. | |
| 46 | Ex. 31 | Et | c-Pr | $CONHCH_2Ph$ | F (10:1) | 0.6 | 236–237° C. | |
| 47 | Ex. 32 | Et | c-Pr | $CONHCH_2$-c-Pr | G (90:10:1) | 0.28 | 205–206° C. | |
| 48 | Ex. 33 | n-Pr | c-Pr | $CONHCH_2Py$ | G (90:10:1) | 0.71 | 163–165° C. | |
| 49 | Ex. 34 | Et | c-Pr | $CONHSO_2Ph$ | F (10:1) | 0.25 | 170–174° C. | |

TABLE 7-continued (see Equation 7)

| Ex. No. | From: | $R^6$ | $R^7$ | $R^8$ | T.l.c. System | Rf = | m.p. | Other |
|---|---|---|---|---|---|---|---|---|
| 66 | Ex. 14 | n-Bu | c-Pr | $CO_2H$ | F (10:1) | 0.25 | 187–189° C. | |

TABLE 8

(see Equation 8)

| Ex. No. | From: | $R^6$ | $R^7$ | $R^8$ | T.l.c. System | Rf = | m.p. | Other |
|---|---|---|---|---|---|---|---|---|
| 50 | Ex. 4 | Et | c-Pr | CONHEt | G(100:10:2) | 0.42 | 155–160° C. | |
| 51 | Ex. 4 | Et | c-Pr | $CONHCH_2CH(CH_3)_2$ | G(200:10:2) | 0.14 | 236–238° C. | |
| 52 | Ex. 16 | n-Pr | c-Pr | CONHEt | G(100:10:5) | 0.36 | 210° C. | |
| 53 | Ex. 16 | n-Pr | c-Pr | $CONHCH_2C(CH_3)_3$ | G(100:10:5) | 0.56 | 197–199° C. | |
| 54 | Ex. 4 | Et | c-Pr | $CONHCH_2CF_3$ | G(80:4:1) | 0.25 | 220–223° C. | |
| 55 | Ex. 4 | Et | c-Pr | $CONHCH_2Ph$ | F(20:1) | 0.2 | 228–232° C. | |
| 56 | Ex. 4 | Et | c-Pr | $CONHCH_2$-c-Hex | G(100:10:1) | 0.4 | 238–240° C. | |
| 57 | Ex. 16 | n-Pr | c-Pr | $CONHCH_2Ph$ | G(100:10:5) | 0.25 | 131–133° C. | |

TABLE 9

| Ex. No. | From: | $R^3$ | $R^4$ | $R^8$ | T.l.c. System | Rf = | m.p. | Other |
|---|---|---|---|---|---|---|---|---|
| 60 | Int. 53 | $CO_2Me$ | F | $CO_2H$ | — | — | — | *16 |
| 61 | Int. 56 | $CO_2Me$ | Cl | $CO_2H$ | — | — | — | *21 |
| 62 | Ex. 60 | $CO_2Me$ | F | $CONH_2$ | C(150:8:1) | 0.4 | 201–203° C. | |
| 63 | Ex. 61 | $CO_2Me$ | Cl | $CONH_2$ | C(150:8:1) | 0.4 | 72–75° C. | |
| 64 | Ex. 62 | $CO_2H$ | F | $CONH_2$ | | | 133–136° C. | n.m.r.*24 |
| 65 | Ex. 63 | $CO_2H$ | Cl | $CONH_2$ | | | 245–248° C. | n.m.r.*25 |

TABLE 10

| Int. No. | $R^6$ | $R^7$ | $R^8$ | Data |
|---|---|---|---|---|
| 57 | n-Pr | c-Pr | $CO_2Et$ | T.l.c. System F (20:1) Rf = 0.46 |
| 58 | $-CH_2$-c-Bu | i-Pr | $CO_2Et$ | m.p. 137–139° C. |
| 59 | n-Pr | c-Bu | $CO_2Et$ | m.p. 116–118° C. |
| 60 | n-Bu | c-Pr | $CO_2Et$ | T.l.c. ether Rf = 0.55 |
| 61 | $-CH_2$-c-Bu | $CF_3$ | $CO_2Et$ | m.p. 126–128° C. *17 |

*1Assay found: C, 63.6; H, 5.9; N, 4.2;
$C_{33}H_{37}BrN_2O_5$ requires: C, 63.8; H, 6.0; N, 4.5%
*2solvent was DMSO instead of DMF
*3Assay found: C, 62.6; H, 5.5; N, 4.4;
$C_{30}H_{31}BrN_2O_5$ requires: C, 62.2; H, 5.4; N, 4.8%
*4Assay Found: C, 62.8, H, 5.75; N, 4.4;
$C_{31}H_{33}BrN_2O_5$ requires: C, 62.7; H, 5.6; N, 4.7%
*5n.m.r. ($CH_3OH$-$d_4$) δ 0.9(7H, m), 1.48(2H, m), 1.97(3H, S), 2.65(2H, m), 2.79(1H, m), 5.81(2H, s), 7.09(1H, m), 7.18(1H, d), 7.3(2H, d), 7.58(2H, m),7.8(2H, m).
*6isolated as the acetate salt.
*7Assay found: C, 50.0; H, 4.1; N, 8.6;
$C_{27}H_{26}BrF_3N_4O_4S$ requires: C, 50.2; H, 4.1; N, 8.65%
*8n.m.r. ($CDCl_3$) δ 0.9–1.05(7H, m), 1.2–1.25(12H, m), 1.63(2H, m), 1.98(1H, m), 2.59(2H, m) 3.45(2H, m), 5.67(2H, s), 6.38(1H, br.t) 7.08(1H, m), 7.23(1H, d), 7.36(1H, d), 7.55(2H, m), 7.69(1H, m), 7.92(1H, m).
*9n.m.r. ($CDCl_3$) δ 0.85–0.95(7H, m), 1.3(9H, s), 1.4(2H, m), 1.68(4H, m), 2.73(2H, t), 3.45–3.65(8H, br.m), 5.30–5.50(2H, br), 7.05(1H, d), 7.22(1H, s), 7.40(1H, d), 7.5–7.65(2H, m), 7.7(1H, d), 7.93(1H, d).
*10n.m.r. ($CDCl_3$) δ 0.95(3H, t), 1.26(9H, s), 1.67(2H, m), 2.02(2H, m), 2.3(2H, m), 2.55–2.65(4H, m), 3.78(1H, m), 5.5(2H, br.s), 5.63(2H, s), 7.04(1H, m), 7.22(1H, d), 7.37(1H, d), 7.56(2H, m), 7.69(1H, m), 7.93(1H, m).
*11n.m.r. ($CDCl_3$) δ 0.95(3H, t), 1.18(3H, t), 1.25(9H, s), 1.65(2H, m), 1.9–2.1(2H, m), 2.28(2H, m), 2.51(2H, m), 2.66(2H, m), 3.4(2H, m), 3.68(1H, m), 5.57–5.6(3H, m), 7.08(1H, m), 7.26(1H, d), 7.36(1H, d), 7.56(2H, m), 7.69(1H, m), 7.92(1H, m).
*12n.m.r. ($CDCl_3$) δ 0.24(2H, m), 0.52(2H, m), 0.98–1.08(4H, m), 1.2(3H, t), 1.25(9H, s), 2.02(1H, m), 2.64(2H, q), 3.28(1H, m), 5.67(2H, s), 6.58(1H, br.t), 7.08(1H, m), 7.24(1H, d), 7.36(1H, d), 7.5–7.6(2H, m), 7.67(1H, m), 7.92(1H, m).
*13n.m.r ($CDCl_3$) δ 0.92(3H, t), 1.02–1.07(4H, m), 1.25(9H, b), 1.64(2H, m), 1.98(1H, m), 2.59(2H, m), 3.44(2H, m), 5.67(2H, s), 6.38(1H, br.t), 7.08(1H, m), 7.23(1H, d), 7.37(1H, d), 7.55(2H, m), 7.69(1H, m), 7.93(1H, m).
*14n.m.r ($CDCl_3$) δ 1.1–1.3(16H, m), 2.24(1H, m), 2.62(2H, q), 5.55(2H, s), 6.88(1H, dd), 7.1(1H, s), 7.28(1H, s), 7.46–7.62(5H, m), 7.69(1H, d), 7.93(1H, d), 8.07(2H, d), 9.16(1H, br.s).
*15n.m.r. ($CDCl_3$) δ 0.9–1.1(4H, m), 1.18(3H, t), 1.28(3H, t), 1.6(9H, s), 2.58–2.7(3H, m), 4.25(2H, q), 5.58(2H, s), 6.9–7.0(2H, m), 7.14(1H, br.s), 7.35–7.42(3H, m), 7.68(1H, dd).
*16used without isolation - see Ex 62.

TABLE 10-continued

| Int. No. | R⁶ | R⁷ | R⁸ | Data |
|---|---|---|---|---|

*[17]initially isolated as

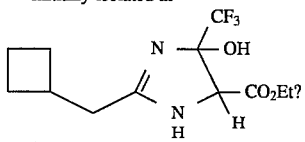

and subsequently dehydrated as described in Intermediate 62 to give the required imidazole.

*[18]Intermediate 36 is an imidazole-5-carboxaldehyde derivative which is converted to the acid as described in Intermediate 68.

*[19]n.m.r. (CDCl₃) δ 1.24–1.33(9H, m), 1.68–1.88(4H, m), 1.97–2.08(2H, m), 2.69(1H, m), 2.81(2H, m), 3.62(1H, m), 4.23(2H, q), 5.63(2H, s), 7.02(1H, m), 7.12(1H, d), 7.4–7.56(3H, m), 7.69(1H, m), 7.83(1H, m).

*[20]n.m.r. (DMSOd₆) δ 0.85–0.95(4H, m), 1.13(3H, t), 1.47(9H, s), 2.5–2.7(3H, m), 3.8(3H, s), 5.65(2H, s), 7.15(1H, dd), 7.28(1H, br.s), 7.68–7.85(3H, m), 8.14(1H, dd).

*[21]used without purification - see Ex. 61.

*[22]n.m.r. (CDCl₃) δ 0.18(2H, m), 0.55(2H, m), 1.05(1H, m), 2.63(2H, d), 5.69(2H, s), 7.05(1H, dd), 7.21(1H, d), 7.44(1H, ddd), 7.55(1H, ddd), 7.68(1H, dd), 7.70(1H, br.s), 7.82(1H, dd).

*[23]n.m.r. (CDCl₃) δ 0.18(2H, m), 0.55(2H, m), 1.05(1H, m), 2.62(2H, d), 5.68(1H, br.s), 5.77(2H, s), 6.68(1H, br.s) 7.06(1H, dd), 7.22(1H, d), 7.43(1H, d), 7.45(1H, ddd), 7.55(1H, ddd), 7.69(1H, dd), 7.84(1H, dd), 8.0(1H, br.s).

*[24]n.m.r.(DMSOd₆) δ 0.9(2H, m), 1.4(3H, t), 2.16–2.21(1H, m), 2.92(2H, br.q), 5.7(2H, br.s), 7.23(1H, d), 7.4–7.8(5H, m), 7.8–8.0(2H, m).

*[25]n.m.r. (CD₃OD) δ 0.95(2H, m), 1.15–1.3(5H, m), 2.1–2.25(1H, m), 3.05(2H, q), 5.77(2H, br.s), 7.32(H, dd), 7.5–7.7(4H, m), 7.9(1H, dd).

*[26]Assay found C. 50.55; H, 4.3; N, 8.1;
$C_{28}H_{28}BrF_3N_4O_4S.0.3H_2O$ requires C. 51.0; H, 4.4; N, 8.5%

The following further Examples have also been made:

INTERMEDIATE 79

2-(5-Methyl-2-benzofuranyl)benzoic Acid

Intermediate 7 (10.0 g) was suspended in glycerol and heated to 120° C. under an atmosphere of nitrogen. Solid potassium hydroxide (12.0 g) was added, in portions, and the reaction mixture was heated to 170° C. After 3 hours the mixture was cooled and poured into water (200 ml). 2M hydrochloride acid (100 ml) was added dropwise, with stirring, to the solution. The resulting yellowish solid was isolated by filtration and dried in vacuo to afford the title compound (12.05 g).

T.l.c. hexane:ethyl acetate:acetic acid (15:5:1) Rf=0.43

INTERMEDIATE 80

(±)-3-Chloro-5-methylspiro[benzofuran-2(3H),1'(3'H)-isobenzofuran]- 3'-one

Intermediate 79 (11.95 g) was dissolved in 1,4-dioxane (300 ml) and water (4 ml) was added. The mixture was placed under an atmosphere of nitrogen. N-chlorosuccinimide (7.67 g) was added to the stirred solution which was then heated at reflux for 1.5 hours. The mixture was cooled to room temperature, diluted with ethyl acetate (300 ml) and washed with brine (3×300 ml). The organic solution was concentrated in vacuo to afford a solid (20.2 g) which was triturated with methanol (350 ml) and filtered to give the title compound (7.22 g) as a white solid.

T.l.c. System J (1:3) Rf=0.49.

INTERMEDIATE 81

2-(3-Chloro-5-methyl-2-benzofuranyl)benzoic Acid

Intermediate 80 (7.135 g) was suspended in toluene (250 ml) and 1,8-diazabicyclo[5.4.0]undec-7-ene (4.58 g) was added slowly over a five minute period. The suspension was warmed to 45° C. and stirred for 3 hours. The solution was then heated at reflux for 1 hour. The reaction mixture was cooled, diluted with toluene (500 ml) and shaken with hydrochloric acid (250 ml) and brine (250 ml). The organic layer was dried and concentrated in vacuo to afford the title compound (6.78 g) as a yellow solid.

T.l.c. hexane:ethyl acetate:acetic acid (15:5:1) Rf=0.50

INTERMEDIATE 82

1,1-Dimethylethyl [2-(3-chloro-5-methyl-2-benzofuranyl)phenyl] carbamate

From Intermediate 81 according to the method of Intermediate 5.

T.l.c. System A (1:16) Rf=0.25.

INTERMEDIATE 83

1,1-Dimethylethyl [2-[5-(bromomethyl)-3-chloro-2-benzofuranyl] phenyl]carbamate

From Intermediate 82 according to the method of Intermediate 6.

T.l.c. System A (1:10 ) Rf=0.25

INTERMEDIATE 84

Ethyl 1-[[3-chloro-2-[2-[[(1,1-dimethylethoxy)carbonyl]amino]phenyl]-5-benzofuranyl]methyl]-4-cyclopropyl-2-ethyl-1H-imidazole- 5-carboxylate From Intermediate 13 and Intermediate 83 according to the method of Intermediate 19.

T.l.c. System A (2:3) Rf=0.26

INTERMEDIATE 85

Ethyl 1-[[2-(2-aminophenyl)-3-chloro-5-benzofuranyl] methyl]- 4-cyclopropyl-2-ethyl-1H-imidazole-5-carboxylate From Intermediate 84 according to the method of Intermediate 23.

T.l.c. System A (1:1) Rf=0.29

INTERMEDIATE 86

2,2,2-Trifluoro-1-[5-methyl-2-[(2-nitrophenyl)methoxy]phenyl] ethanone

A solution of 2-nitro benzyl alcohol (6.9 g) in 1,4-dioxane (100 ml) was added to a mixture of 2,2,2-trifluoro-1-[2-hydroxy-5methyl)phenyl] ethanone (described in European Patent Specification No. 0434249-A, published 26 Jun. 91) (6.23 g), sodium iodide (0.458 g) and potassium carbonate (4.64 g) in N,N-dimethylacetamide (60 ml). After stirring for 18 h, distilled water (500 ml) was added and the resultant slurry stirred for 2 h. The solid was collected by filtration, washed with 1,4-dioxane/water (1:1) (300 ml), water (3×50 ml) and oven dried to give the title compound as a pale yellow solid (7.37 g).

T.l.c. System A (1:6) Rf 0.38

INTERMEDIATE 87

2,3-Dihydro-5-methyl-2-(2-nitrophenyl)-3-(trifluoromethyl)-3-benzofuranol (cis & trans Diastereoisomers)

Sodium methoxide (246 mg) was added to a cooled (0° C.) solution of the Intermediate 86 (4,363 g) in N,N-dimethylacetamide (40 ml) and stirred for 3 h. Distilled water (100 ml) was added and the aqueous layer extracted with ethyl acetate (2×100 ml; 80 ml). The combined organic extracts were washed with water (80 ml) and 10% aqueous lithium chloride solution (2×100 ml), dried and the solvent removed in vacuo to give an oil. Purification by flash column chromatography eluting with System A (1:10→1:3) gave the title compounds as pale yellow solids (1.33 g; 2.11 g).

T.l.c. System A (1:3) Rf 0.42 and Rf 0.21

INTERMEDIATE 88

5-(Bromomethyl)-2-(2-nitrophenyl)-3-(trilfluoromethyl)benzofuran

A solution of the diastereoisomers of Intermediate 87 (5.727 g) in acetic anhydride (50 ml) and conc. sulphuric acid (5 drops) was heated at reflux for 4.5 h. After cooling the solution was concentrated in vacuo, diluted with ethyl acetate (100 ml), washed with 8% sodium bicarbonate (2×100 ml) and dried. The solvent was removed in vacuo to give the title compound as a brown solid (5.69 g).

T.l.c. System A (1:1) Rf 0.61

INTERMEDIATE 89

5-(Bromomethyl)-2-(2-nitrophenyl)-3-(trifluoromethyl)benzofuran

From Intermediate 88 according to the method of Intermediate 11.

T.l.c. System A (1:3) Rf=0.33.

INTERMEDIATE 90

Ethyl 4-cyclopropyl-2-ethyl-1-[[2-(2-nitrophenyl)-3-(trifluoromethyl)-5-benzofuranyl]methyl]-1H-imidazole-5-carboxylate Sodium hydride (60% dispersion, 0.5 g) was added to a stirred solution of Intermediate 13 (2.4 g) in DMF (100 ml). After stirring for 45 min under nitrogen, a solution of Intermediate 89 (2.8 g) in DMF (50 ml) was added dropwise. The reaction was stirred at room temperature for 12 h before being diluted with water (800 ml) and extracted with ethyl acetate (500 ml). The organic extract was washed with aqueous lithium chloride (3×200 ml), dried and concentrated in vacuo to afford a residue. This residue was purified by flash column chromatography eluting with System F (50:1)→(30:1) to give the title compound (1.6 g) as a brown foam.

T.l.c. System F (15:1) Rf=0.4.

INTERMEDIATE 91

Ethyl 1-[[2-(2-aminophenyl)-3-(trifluoromethyl)-5-benzofuranyl]methyl]-4-cyclopropyl-2-ethyl-1H-imidazole-5-carboxylate A mixture of 10% palladium on carbon (1 g), water (30 ml), conc. hydrochloric acid (30 ml) and a solution of Intermediate 90 (1.4 g) in THF (90 ml) was hydrogenated at room temperature for 2 h. The mixture was filtered through 'hyflo' and the filtrate was evaporated in vacuo. The residue was dissolved in dichloromethane (100 ml) washed with sodium carbonate (2N; 500 ml), dried and evaporated. The residue was purified by flash column chromatography eluting with System F (75:1) to give the title compound as an off-white foam (1.03 g).

T.l.c. System A (1:1) Rf=0.23.

EXAMPLE 78

Ethyl 1-[[3-chloro-2-[2-[[(trifluoromethyl)sulphonyl]amino]phenyl]-5-benzofuranyl]methyl]-4-cyclopropyl-2-ethyl-1H-imidazole-5-carboxylate From Intermediate 85 according to the method of Example 3.

T.l.c. ether:acetic acid (200:1) Rf=0.63 n.m.r. (CDCl$_3$) δ0.97 (2H,m), 1.8(2H,m), 1.2 (3H,t), 1.3 (3H,t), 2.58–2.72 (3H,m), 5.64 (2H,s), 7.08 (1H,m), 7.3 (1H,m), 7.41–7.56 (3H,m), 7.7 (1H,m), 7.85 (1H,m).

EXAMPLE 79

1-[[3-Chloro-2-[2-[[(trifluoromethyl)sulphonyl]amino]phenyl]-5-benzofuranyl]methyl]-4-cyclopropyl-2-ethyl-1H-imidazole-5-carboxylic Acid From the product of Example 78 according to the method of Example 5. m.p. 164°–165° C. (decomp)

T.l.c. ethyl acetate Rf=0.46 (streak).

EXAMPLE 80

1-[[3-Chloro-2-[2-[[(trifluoromethyl)sulphonyl]amino]phenyl]-5-benzofuranyl]methyl]-4-cyclopropyl-2-ethyl-1H-imidazole-5-carboxamide From the product of Example 79 according to the method of Intermediate 26 followed by the method of Example 6.

T.l.c. System J (1:3) Rf=0.28 n.m.r. (CDCl$_3$) δ 1.0–1.1 (4H,m), 1.27 (3H,t), 1.95–2.05 (1H,m), 2.66 (2H,q), 5.69 (2H,s), 7.1 (1H,m), 7.27–7.3 (1H,m), 7.4–7.56(3H,m), 0.7 (1H,m), 7.84 (1H,m).

EXAMPLE 81

Ethyl 1-[[3-(trifluoromethyl)-2-[2-[[(trifluoromethyl)sulphonyl]amino]phenyl]-5-benzofuranyl]methyl]-4-cyclopropyl-2-ethyl-1H-imidazole- 5-carboxylate From Intermediate 91 according to the method of Example 3.

T.l.c. ether Rf=0.65 n.m.r. (CDCl$_3$) δ 0.9–1.1 (m, 4H), 1.18 (t,3H), 1.3 (t,3H), 2.55–2.7 (m,3H), 4.27 (q,2H), 5.2–5.6 (vbr.s, 1H), 5.62 (br.s, 2H), 7.03 (dd,1H), 7.4–7.75 (m, 6H).

EXAMPLE 82

1-[[3-(Trifluoromethyl)-2-[2-[[(trifluoromethyl)sulphonyl]amino]phenyl]-5-benzofuranyl]methyl]-4-cyclopropyl-2-ethyl-1H-imidazole-5-carboxylic Acid From the product of Example 81 according to the method of Example 5. m.p. 155°–158° C.

T.l.c. System G (20:2:1) Rf=0.3

EXAMPLE 83

1-[[3-(Trifluoromethyl)-2-[2-[[(trifluoromethyl)sulphonyl]amino]phenyl]-5-benzofuranyl]methyl]-4-cyclopropyl-2-ethyl-1H-imidazole-5-carboxamide From the product of Example 82 according to the method of Intermediate 26 followed by the method of Example 6. m.p. 183°–186° C.

T.l.c System F (10:1) Rf=0.47

We claim:

1. A compound of formula (I):

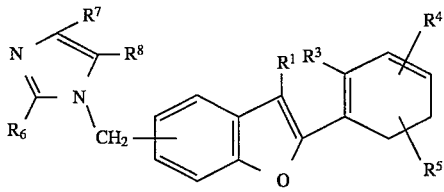

or a physiologically acceptable salt or hydrate thereof wherein:

$R^1$ represents a hydrogen atom, a halogen atom, $C_{1-6}$alkyl, $C_{2-6}$alkenyl, fluoro$C_{1-6}$alkyl, $C_{1-6}$alkoxy, —CHO, —CO$_2$H or —COR$^2$;

$R^2$ represents $C_{1-6}$alkyl, $C_{2-6}$alkenyl, $C_{1-6}$alkoxy or —NR$^{13}$R$^{14}$;

$R^3$ represents —CO$_2$H, —NHSO$_2$CF$_3$ or a C-linked tetrazolyl group;

$R^4$ and $R^5$ which may be the same or different each independently represent a hydrogen atom or a halogen atom or a $C_{1-6}$alkyl group;

$R^6$ represents a $C_{1-5}$alkyl group;

$R^7$ represents a cyclopropyl, cyclobutyl or cyclopropylmethyl group;

$R^8$ represents —CH$_2$OH, —CHO, —CH$_2$OCH$_3$, —CO$_2$H, —CO$_2$CH$_3$, —CO$_2$CH$_2$CH$_3$, —CONH$_2$, —CONHCH$_3$ or —CONHCH$_2$CH$_3$; and $R^{13}$ and $R^{14}$, which may be the same or different, each independently represent a hydrogen atom or a $C_{1-4}$alkyl group, or —NR$^{13}$R$^{14}$ forms a saturated heterocyclic ring which has 5 or 6 ring members.

2. A compound according to claim 1 wherein $R^6$ represents an ethyl, n-propyl or n-butyl group.

3. A compound according to claim 1 wherein $R^6$ represents an ethyl group.

4. A compound according to claim 1 wherein $R^1$ represents a hydrogen atom, a halogen atom, $C_{1-6}$alkyl, $C_{1-6}$alkoxy or fluoro$C_{1-6}$alkyl.

5. A compound according to claim 1 wherein the group

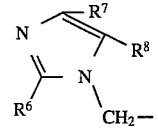

is attached at the 5- or 6- position on the benzofuran ring.

6. A compound according to claim 1 wherein $R^4$ and $R^5$ each independently represent a hydrogen atom or a halogen atom.

7. A compound which is:

1-[[3-Bromo-2-[2-[[(trifluoromethyl)sulphonyl]amino]phenyl]-5-benzofuranyl]methyl]- 4-cyclopropylmethyl-2-ethyl-1H-imidazole-5-carboxamide;

1-[[3-Bromo-2-[2-[[(trifluoromethyl)sulphonyl]amino]phenyl]-5-benzofuranyl]methyl]- 4-cyclopropylmethyl-2-ethyl-N-methyl-1H-imidazole-5-carboxamide;

1-[[3-Bromo-2-[2-[[(trifluoromethyl)sulphonyl)amino]phenyl]-5-benzofuranyl]methyl]- 4-cyclopropylmethyl-N,2-diethyl-1H-imidazole-5-carboxamide;

1-[[3-Bromo-2-[2-[[(trifluoromethyl)sulphonyl]amino]phenyl]-5-benzofuranyl]methyl]- 4-cyclobutyl-2-ethyl-1H-imidazole-5-carboxamide;

1-[[3-Bromo-2-[2-[[(trifluoromethyl)sulphonyl]amino]phenyl]-5-benzofuranyl]methyl]- 4-cyclobutyl-2-ethyl-N-methyl-1H-imidazole-5-carboxamide;

1-[[3-Bromo-2-[2-[[(trifluoromethyl)sulphonyl]amino]phenyl]-5-benzofuranyl]methyl]- 4-cyclobutyl-N,2-diethyl-1H-imidazole-5-carboxamide;

1-[[3-Bromo-2-[2-(1H-tetrazol-5-yl)phenyl]-5-benzofuranyl]methyl]- 4-cyclopropyl-2-ethyl-1H-imidazole-5-carboxylic acid;

1-[[3-Bromo-2-[2-(1H-tetrazol-5-yl)phenyl]-5-benzofuranyl]methyl]- 4-cyclobutyl-2-ethyl-1H-imidazole-5-carboxylic acid;

1-[[3-Bromo-2-[2-(1H-tetrazol-5-yl)phenyl]-5-benzofuranyl]methyl- 4-cyclopropylmethyl-2-ethyl-1H-imidazole-5-carboxylic acid;

1-[[3-Bromo-2-[2-[[(trifluoromethyl)sulphonyl]amino]phenyl]-5-benzofuranyl]methyl]- 4-cyclopropyl-2-ethyl-N-methyl-1H-imidazole-5-carboxamide;

1-[[3-Bromo-2-[2-[[(trifluoromethyl)sulphonyl]amino]phenyl]-5-benzofuranyl]methyl]- 4-cyclopropyl-N,2-diethyl-1H-imidazole-5-carboxamide;

or a physiologically acceptable salt, solvate or metabolically labile ester thereof.

8. A pharmaceutical composition comprising at least one compound of formula (I) as defined in claim 1 or a physiologically acceptable salt, solvate or metabolically labile ester thereof, together with at least one physiologically acceptable carrier or excipient.

9. A method for treatment of hypertension which method comprises administering to a patient in need of such treatment an effective amount of a compound of formula (I) as claimed in claim 1 or a physiologically acceptable salt, or hydrate thereof.

10. A compound according to claim 4 wherein $R^1$ represents a hydrogen atom, a halogen atom, or a $C_{1-3}$alkyl group.

11. A compound according to claim 10 wherein $R^1$ represents a bromine atom.

12. A compound according to claim 5 wherein the group

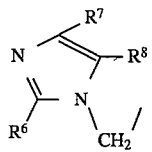

is attached at the 5-position on the benzofuran ring.

13. A compound according to claim 6 wherein $R^4$ and $R^5$ each represent a hydrogen atom.

14. A method for treatment of excessive angiotensin II activity, which method comprises administering to a patient in need of such treatment an effective amount of a compound of formula (I) as claimed in claim 1 or a physiologically acceptable salt or hydrate thereof.

15. A method for treatment of unregulated angiotensin II activity, which method comprises administering to a patient in need of such treatment an effective amount of a compound of formula (I) as claimed in claim 1 or a physiologically acceptable salt or hydrate thereof.

16. The compound of claim 7 which is 1-[[3-Bromo-2-[2-[ [(trifluoromethyl)sulphonyl]amino]phenyl]-5-benzofuranyl]methyl]-4-cyclopropyl-2-ethyl-N-methyl- 1H-imidazole-5-carboxamide.

* * * * *